United States Patent [19]

Condra

[11] Patent Number: 4,973,551
[45] Date of Patent: Nov. 27, 1990

[54] VECTOR FOR THE EXPRESSION OF FUSION PROTEINS AND PROTEIN IMMUNOGENS

[75] Inventor: Jon H. Condra, Abington, Pa.

[73] Assignee: Merck & Co., Inc., Rahway, N.J.

[21] Appl. No.: 145,800

[22] Filed: Jan. 15, 1988

[51] Int. Cl.$^5$ .................. C12P 21/06; C12P 21/04; C12P 19/34; C12N 15/00; C12N 1/20; C12H 15/12; C07K 3/00

[52] U.S. Cl. .................. 435/69.7; 435/71.1; 435/91; 435/172.1; 435/172.3; 435/252.33; 435/320; 536/27; 530/350; 935/10; 935/29; 935/45; 935/47; 935/56; 935/73

[58] Field of Search ............ 435/69, 91, 172.1, 172.3, 435/252.33, 320; 530/351; 536/27; 935/6, 31, 41, 58, 60, 73

[56] References Cited

U.S. PATENT DOCUMENTS 4,639,372 1/1987 Murray et al. .
4,650,676 3/1987 Schenkel et al. .
4,710,377 12/1987 Schenkel et al. .

FOREIGN PATENT DOCUMENTS 164176 12/1985 European Pat. Off. .
241139 10/1987 European Pat. Off. .
WO86/00528 1/1986 PCT Int'l Appl. .

OTHER PUBLICATIONS

Aviv and Leder, Proc. Natl. Acad. Sci. U.S.A. 69: 1408–1412 (1972).
Bethell et al. J. Biol. Chem. 254: 2572–2574 (1979).
Bhanushali and Long, in "Research in Avian Coccidiosis," McDougald et al. eds., Proceedings of Georgia Coccidiosis Conf., pp. 526≧534 (1985).
Chirgwin et al., Biochem. 18: 5294–5299 (1979).
Clarke et al., Mol. and Biochem. Parasit, 22: 79–87 (1987).
Corthier et al., J. Immunol. Meth. 66: 75–79 (1984).
Crane et al., Infect. Immun. 56: 972–976 (1988).
Davis et al., Basic Methods in Molecular Biology, Elsievier, New York, N.Y. p. 30 (1986).
Edgar, Trans. Am. Micr. Soc. 62: 237–242 (1954).
Gubler and Hoffman, Gene 25: 263–269 (1983).
Hall et al., Nature 311: 379–382 (1984).
Hattori and Sakaki, Anal. Biochem. 152: 232–238 (1986).
Huynh et al., In "DNA Cloning: a Practical Approach," vol. I, Glover Ed., IRL Press, Oxford, pp. 49–78 (1985).
Ish-Horowicz and Burke, Nucleic Acids Research 9: 2989–2998 (1981).
Jackson, Parasitol. 54: 87–93 (1964).
Kohler and Milstein, Nature 256: 495–497 (1975).
Laemmli, Nature 227: 680–684 (1970).
Long et al., Biol. Abst. 75, No. 3, p. 1904, Ref. 18594 (1982).
Lowry et al., J. Biol. Chem. 193: 265–275 (1951).
MacPherson, Soft Agar Techniques, in "Tissue Culture Methods and Applications", Academic Press, pp. 276–277 (1973).
Maniatis et al., Molecular Cloning, a Laboratory Manual, Cold Spring Harbor Lab., pp. 202–203 and 468–469 (1982).
Mason and Williams, in "Nucleic Acid Hybridization: a Practical Approach" Hames and Higgens, Eds., IRL Press, pp. 113–137 (1985).
Matsumura et al., J. Bactol. 160: 36–41 (1984).

(List continued on next page.)

*Primary Examiner*—Robin L. Teskin
*Assistant Examiner*—Joan Ellis
*Attorney, Agent, or Firm*—Jack L. Tribble; Hesna J. Pfeiffer

[57] ABSTRACT

An expression vector which can be used to express fusion proteins which are useful as immunogens. The vector is characterized as a 3.35 kilobase pair vector having origins for replication and selectivity markers for bacteria. The plasmid has an *E. coli* promotor segment, a CheY fusion protein sequence and a unique restriction site at the 3' end of the CheY segment for preparing a DNA segment which codes for a foreign protein to be expressed.

4 Claims, 8 Drawing Sheets

OTHER PUBLICATIONS

Maxam and Gilbert, Methods in Enzymology 65: (part 1): 499–559 (1980).
Messing, Methods in Enzymology 101: 20–78 (1983).
O'Farrell, J. Biol. Chem. 250: 4007–4021 (1975).
Okayama and Berg, Mole. Cell. Biol. 2: 161–170 (1982).
Old and Primrose, Principles of Gene Manipulation: University of California Press, p. 20 (1981).
Patton, Science 150: 767–769 (1965).
Patton et al., J. Parasito. 5: 526–530 (1979).
Rose and Kesketh, Parasitol. 73: 25–37 (1976).
Santoro et al., J. Biol. Chem. 258: 3341–3345 (1983).
Schmatz et al., J. Protozool. 31: 181–183 (1984).
Schneider et al., J. Biol. Chem. 257: 10766–10769 (1982).
Smithies et al., Science 202: 1284–1289 (1978).
Tabor and Richardson, Proc. Natl. Acad. Sci. U.S.A. 84: 4767–4771 (1987).
Taylor et al., Mol. Biochem. Parasitol. 10: 305–318 (1983).
Temeles et al., Nature 313: 700–703 (1985).
Towbin et al., Proc. Natl. Acad. Sci. U.S.A. 76: 4350–4354 (1979).
Weir, Handbook of Experimental Immunology Blackwell Scientific Publ. London, pp. A3.11–A3.15 (1978).
Wisher, Mol. Biochem. Parasitol. 21: 7–15 (1986).
Yanisch-Perron et al., Gene 33:103–119 (1985).
James, Parasitol. 80: 301–312 (1980).
Johnson and Reid, Exp. Parasitol. 28: 30–36 (1970).

VECTOR FOR THE EXPRESSION OF FUSION PROTEINS AND PROTEIN IMMUNOGENS

BACKGROUND OF THE INVENTION

Figure 1:
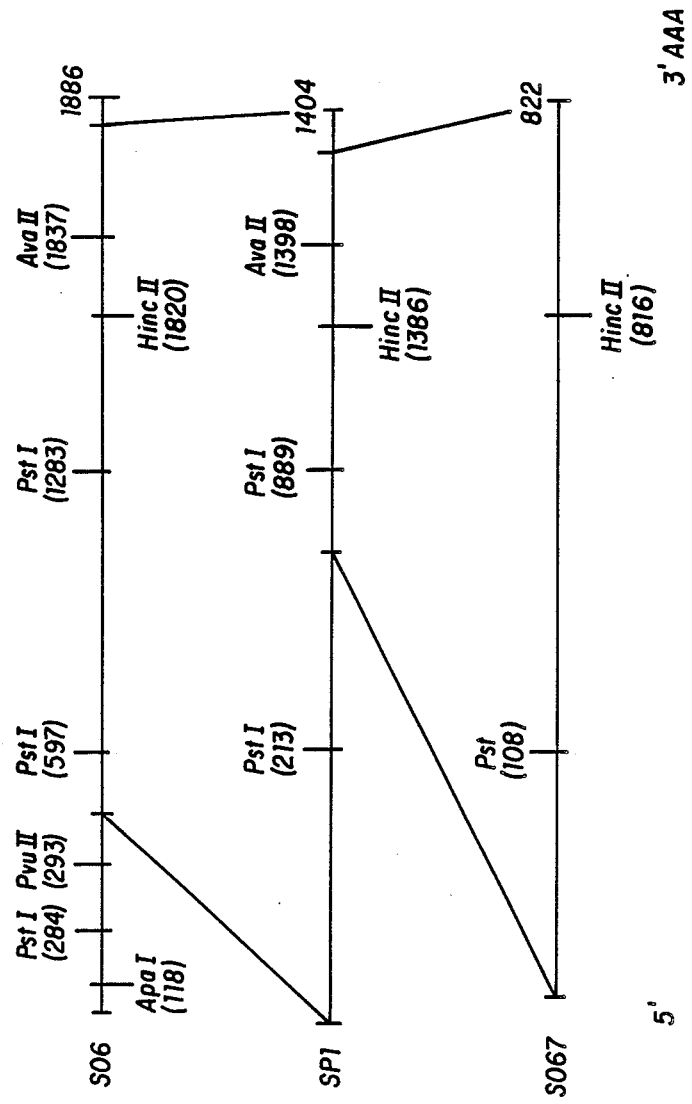
FIG. 1 is a restriction map of group A 21 clones.

Coccidiosis is a disease caused by infection with one or more of the many species of coccidia, a subdivision of the phylum Protozoa. The coccidia are intracellular parasites which can infect a wide range of hosts and may result in severe economic loss to the sheep, goat, cattle, swine and poultry industry. Indeed, coccidiosis resulting from infection with Eimeria species has caused economically devasting losses to the poultry industry. Poultry is defined herein as domesticated birds that serve as a source of eggs or meat and that include among commercially important kinds chickens, turkeys, ducks, geese, guinea fowl, pheasants, pigeons and peafowl. Among domesticated birds, chicken production is the most susceptible to the economic losses from coccidiosis, although losses can also occur with turkeys, geese, ducks, and guinea fowl. Coccidiosis also produces serious losses in pheasants and quail raised in captivity. Coccidiosis may be acute and characterized by devastating flock mortality or the disease may be chronic and characterized by lack of weight gain.

Poultry are infected by coccidia following ingestion of the vegetative stage of the parasite, the sporulated oocyst. The infective stage, the sporozoite, is released in the intestine where it rapidly invades epithelial cells subsequently under going several generations of rapid intracellular asexual multiplication (schizogony) before entering the stage of sexual differentiation and mating (gametogony) leading to the formation of immature oocysts which are shed in the droppings and then undergo an extracellular sporulation process (sporogony) resulting in the generation of mature oocysts. Low level infection with any of the Eimeria species (spp.), *E. acervulina, E. mivati, E. mitis, E. praecox, E. hagani, E. necatrix, E. maxima, E. brunetti* and *E. tenella* results in a protective immunity to reinfection. There may be as many as twelve distinct cell types involved in the development of the parasite, each morphologically and antigenically different. At least three of these cell types have been shown to induce a protective immune responsse in the host, Rose and Hesketh, Parasitol. 73:25-37 (1976), McDonald et al., Parasitol. 93:1-7 (1986), Bhanushali and Long, In, Research in Avian Coccidiosis, Proc. of the Georgia Coccidiosis Conf., Athens, Ga., USA pp. 526-534 (1986). Both the sporozoite as well as the first and second generation schizont appear to contain antigens which elicit an immunizing effect in chickens.

Unlike the sporozoite surface of other parasites such as *Plasmodium falciparum* which is composed of a single dominant antigen, Santoro et al., J. Biol. Chem. 258:3341-3345 (1983), the Eimeria spp., in particular, *E. tenella* sporozoite surface appears to be antigenically complex, Wisher, Mol. Biochem. Parasitol. 21:7-15 (1986). Because the sporozoite stage cannot be cultivated in vitro and large amounts of sporozoite material would be necessary for conventional biochemical analysis and for subunit vaccine evaluation, the purification of these antigens has posed a problem. A subunit vaccine as used herein is defined as a peptide, polypeptide or protein which is either isolated from one or more of the life stages of any species of Eimeria or is produced by recombinant DNA technology and which either individually or combined with other such peptides, polypeptides or proteins induces a protective immunity in poultry following vaccination. The recombinant antigens or immunogens will be the same as or similar to the peptides, polypeptides or proteins isolated from one or more life stages of Eimeria. Immunogen is defined as a substance that when introduced into the body stimulates an immune response which is protective in nature, such as the use of a vaccine to produce immunity against a microorganism. Immunity is defined as the non susceptibility to the invasive or pathogenic effects of foreign organisms or the toxic effects of products of foreign organisms. The protective immunity may be either humoral or cell mediated immunity. Humoral immunity is defined as specific immunity mediated by antibodies which are present in the plasma, lymph and tissue fluids of the body, and which may become attached to cells. Cell mediated immunity is defined as specific immunity mediated by T lymphocytes. Antigen is used herein to define a substance capable of specifically combining with specific antibody.

Solubilized *E. tenella* sporozoite proteins, identified by monoclonal antibodies prepared against intact *E. tenella* sporozoites, have been shown to protect chickens against challenge with infective oocysts, Schenkel et al., European Patent Application Number 135,712 Similar results were obtained with *E. tenella* merozoites prepared by the same techniques, Schenkel et al. European Patent application No. 135,073. Immunogenic polypeptides have been isolated from *E. tenella* sporozoites, Murray and Galuska, U.S. Pat. No. 4,639,372. There was no indication, however, that any individual polypeptide would protect chickens against *E. tenella* challenge.

Recombinant DNA technology has allowed for the identification of immunogenic Eimeria polypeptides and for the production of the polypeptides in sufficient quantities for vaccine development. Newman et al., European Patent Application 164,176, describe the isolation of a 25,000 dalton polypeptide from *E. tenella* which is made up of two subunits of 17,000 and 8,000 daltons respectively. The 25,000 dalton polypeptide has been produced by recombinant DNA technology utilizing a genomic DNA clone and has been shown to protect chickens against coccidiosis caused by E. tenella. Another immunogenic *E. tenella* polypeptide has been disclosed by Anderson and McCandliss, Patent Cooperation Treaty Application WO 86/00528. This peptide has been sequenced and is composed of 280 amino acids, has been produced by recombinant DNA technology utilizing both an oocyst genomic DNA clone and a clone isolated from total oocyst mRNA, and protects chickens against coccidiosis. Clark et al., Mol. and Biochem. Parasit. 22:79-87 (1987), recently disclosed the construction of genomic DNA expression libraries from *E. tenella* in *Escherichia coli* using the expression vector λamp3. Clones expressing *E. tenella* immunogens were detected but none of the peptides were tested for immunogenic activity. *Eimeria tenella* sporozoite surface membranes have been labeled by various techniques to characterize potential surface immunogens, Wisher, Mol. Biochem. Parasit, 21:7-15 (1986). The major surface polypeptides which reacted with anti-*E. tenella* antibody were in the following ranges: 113-96 kD, 73-67 kD, 54-42 kD, 37-32 kD, and 18-14 kD.

SUMMARY OF THE INVENTION

An expression vector which can be used to express fusion proteins which are useful as immunogens. The vector is characterized as a 3.35 kilobase pair vector having origins for replication and selectivity markers for bacteria. The plasmid has an *E. coli* promotor segment, a CheY fusion protein sequence and a unique restriction site at the 3' end of the CheY segment for preparing a DNA segment which codes for a foreign protein to be expressed.

OBJECT OF THE INVENTION

It is accordingly, an object of the present invention to provide novel proteins of *Eimeria tenella* which can be used to immunize chickens against coccidiosis. Another object is to provide immunogenic proteins specifically associated with sporulated oocysts and sporozoites. A further object is to provide the deduced amino acid sequence of the immunogenic proteins. Another object is to isolate genes coding for the specific protein immunogens and to incorporate the genes into appropriate expression vectors. A further object is to transform an appropriate host with each of the recombinant vectors, to induce expression of the specific coccidial genes and to isolate the pure immunogens. Another object is to produce a novel expression vector for the expression of the specific coccidial proteins. A further object is to produce monospecific antibodies reactive against the immunogenic proteins.

DETAILED DESCRIPTION OF THE INVENTION

The present invention relates to coccidiosis vaccines based on either native or recombinant-derived purified protein immunogens and any micro heterogeneous or subunit immunogen forms of the protein associated with sporulated oocysts, sporozoites, schizonts and merozoites of *Eimeria tenella*. Native protein as used herein refers to the full length protein produced by the appropriate Eimeria gene in the parasite. Recombinant derived refers to the isolation of a gene for a desired protein and the use of that purified gene to construct a bacterium which will overproduce the desired protein. Subunit immunogen forms is defined as a portion of an immunogenic protein or polypeptide which has fewer amino acids than the native immunogenic moiety but contains the immunogenic site or sites of the immunogen. Microheterogeneous forms as used herein refers to a single gene product, that is a protein produced from a single gene unit of DNA, which is structurally modified following translation. These structural modifications, however, do not result in any significant alterations of the immunogenic activity of the protein. The modifications may take place either in vivo, in the parasite, or during the isolation and purification process. In vivo modification may result in, but is not limited to, acetylation at the N terminus, proteolysis, glycosylation or phosphorylation. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which may result in the production of microheterogeneous forms. The most common modification occuring during purification is proteolysis which is generally held to a minimum by the use of protease inhibitors.

The invention further relates to isolation and purification of the genetic information responsible for individual protein and the methods of expressing the corresponding immunogenic proteins. Polypeptide or protein as used herein refers to a linear polymer of amino acids bound together with amide linkages. The sequence of amino acids in the chain is of critical importance in the biological functioning of the protein or polypeptide. Polypeptide and protein are used interchangeably herein. Immunogen as used herein refers to molecules or macromolecules which when introduced into an animal body stimulates a humoral and/or a cellular immune response which is functional in nature, that is an immunity which protects the animal from a specific infection. In the instant case an immunogen will produce an immune response, either humoral, cellular or both which will protect poultry against infection with Eimeria species which cause coccidiosis.

*Eimeria tenella* oocysts are isolated from the cecal contents of chickens infected 4 to 10 days earlier, preferably 7 days, while *E. acervulina* oocysts are isolated from feces and intestinal contents of chickens infected 5 to 6 days earlier. The cecal contents and feces are individually physically disrupted in a Waring Blender, in distilled water and digested with a proteolytic enzyme, preferably pepsin. Debris and pepsin are removed by centrifugation in distilled water. A partially pure oocyst fraction is collected by flotation in about 2.2M sucrose, Jackson, Parasitol. 54:87-93 (1964), and further treated by incubation in sodium hypochlorite at a concentration of about 5 to about 6 percent, preferably 5.25%, in water at about 4° C. for approximately 10 minutes. The sodium hypo chlorite is removed by several washes in sterile phosphate buffered saline (PBS) at about pH 7.6 to obtain purified, sterile oocysts. Oocysts are allowed to sporulate in a shaking water bath for about 48 hours at about 20° C., Edgar, Trans. Am. Micr. Soc. 62:237-242 (1954).

Sporulated oocysts are suspended in PBS and disrupted in a Bransonic cell disruptor (Branson), with a tapered probe at about 0° C. Sonication is carried out with short bursts, about 30 seconds, to prevent overheating, with 90 percent breakage occuring within about 5 to about 20 minutes. A detergent is added to the sonicate, preferably Zwittergent 3-12 (Calbiochem) about 0.1% w/v and the mixture is stirred at about 4° C. for about 18 hours. The detergent treated sporulated oocyst preparation is centrifuged at about 27,000×g for about 30 minutes and the supernatant fluid collected.

Sporozoites are prepared by grinding a suspension of purified sporulated oocysts, about $5 \times 10^7$/ml in PBS, at about pH 7.6, at about 500 rpm for about 5 minutes at about 4° C. in a tissue homogenizer with a loose-fitting pestle following the procedure of Patton, Science 150:767-769 (1965). The disrupted material is collected by centrifugation. The *E. tenella* pellet consists of unbroken oocysts, sporocysts and oocyst shells which is resuspended in an excysting solution containing about 0.25% (w/v) trypsin and about 4% (w/v) taurodeoxycholic acid (Sigma) in a buffered solution such as Hanks balanced salt solution (pH 7.4). The *E. acervulina* pellet, also composed of unbroken oocysts, sporocysts and oocyst shells, was resuspended in an excysting solution containing about 0.125% (w/v) trypsin (1:250) and about 1.0% taurodeoxycholic acid in a buffered solution such as Hank's Balanced salt solution (pH 7.4). The resuspended pellets are incubated at about 41° C. in an atmosphere containing about 5% $CO_2$. Excysting was allowed to continue for about ½ hour for *E. acervulina* and about 1 hour for *E. tenella* after which time the solutions are removed by centrifugation. Sporozoites are isolated using a DE-52 anion exchange column employing the method of Schmatz et al. J. Protozool. 31:181–183 (1984). Purified sporozoites are disrupted by freezing and thawing at least 3 times, and sonicated until disrupted in PBS containing about 1 mM phenylmethylsulfonylfluoride.

Both the sporulated oocyst and the sporozoite cell free preparations are separated by gel permeation chromatography, preferably Sephadex S 200 (Pharmacia) in a separation buffer containing about 50 mM $Na_2HPO_4$-$NaH_2PO_4$, pH about 7.2 and about 0.1% Zwittergent 3-12. Each preparation is added to the column, about $8 \times 44$ cm and eluted with the separation buffer. Elution is monitored by absorbance at 230 nm and the fractions, about 14 ml per fraction, collected. The fractions are analyzed by linear gradient sodium dodecyl sulfate (SDS) polyacrylamide gel electrophoresis (SDS PAGE) and the fractions pooled according to these profiles. Pooled fractions were dialyzed against a bicarbonate buffer and tested for their ability to protect chickens against challenge with infective *E. tenella* sporulated oocysts. Two day old broiler pullets are immunized intramuscularly with pooled fractions of sporulated oocyst or sporozoite cell free immunogens, about 5 μg to about 50 μg protein in PBS. The cell free immunogen is precipitated to alum (about 0.4% final concentration) in a total volume of about 0.12 ml per dose per bird. The alum-immunogen precipitation complex is prepared by the technique of Weir, Handbook of Experimental Immunology, Blackwell Scientific Publications, London, pg. A3.11 (1978). Immunization was repeated at days nine and sixteen and the birds are challenged on day 23, seven days after the final immunization, with infective *E. tenella* sporulated oocysts. A single fraction from each preparation protected the chickens from sporozoite challenge. These fractions had similar elution and electrophoresis profiles suggesting that the polypeptides may be similar. The most active immunogenic fraction isolated from sporulated oocysts is found in column fractions 84–94 and is designated Fraction V.

Antiserum is produced against the immunoprotective fractions of *Eimeria tenella* sporulated oocysts (Fraction V), sporozoites, sonicated unsporulated oocysts, second generation schizonts and *E. acervulina* sonicated sporozoites. The *E. tenella* schizonts are prepared from chicken intestinal cells about four days post infection according to the protocol of James, Parasitol. 80:301–312 (1980). Blood is collected from the antibody producing animals, preferably rabbits, prior to initiation of the immunization procedure and the preimmune serum is isolated and stored for control purposes. The rabbits are given multiple immunization injections with one of the above described immunogens, about 20 μg to about 80 μg of protein per immunization. The initial immunization is given with an acceptable adjuvant, generally equal volumes of immunogen and adjuvant. Acceptable adjuvants include Freund's complete, Freund's incomplete, alum precipitate, water-in oil emulsion containing *Corynebacterium parvum* and tRNA, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art. The anti coccidial antisera are characterized by serological analysis, preferably Western blot analysis using antigens obtained from unsporulated oocysts, sporulated oocysts, sporozoites and schizonts. Antigen as used herein is defined as any substance that can combine with an antibody. Immunogens as described above are considered antigens when used to characterize the specific antibody.

The parasite immunogens to be used for Western blot analysis, about 50 μg, as described above, are mixed in about equal volumes with about $2 \times$ concentrated sample buffer consisting of about 0.1M Tris HCl, about pH 6.8, about 4% sodium dodecyl sulfate (SDS), about 20% (v/v) glycerol, about 10% (v/v) 2-mercaptoethanol, and about 0.002% (v/v) bromophenol blue. The samples are boiled for about 3 minutes and electrophoresed on a 5–20% linear gradient of polyacrylamide gel (PAGE) containing SDS by the method of Laemmli, Nature 227:680–684 (1970). The proteins separated by SDS PAGE are electrophoretically transfered to nitrocellulose by the method of Towbin et al., Proc. Natl. Acad. Sci. USA 76:4350–4354 (1979), and the nitrocellulose is blocked with 0.5% gelatin in phosphate buffered saline about pH 7.4. The blocked nitrocellulose is incubated overnight at room temperature in about 20 ml of the appropriate antiserum diluted about 1:5 to 1:400 in TEN buffer (about 50 mM Tris HCl, about 150 mM NaCl and about 5 mM ethylenediamine tetraacetic acid (EDTA) at a pH of about 7.4) containing about 0.25% gelatin and 0.05% Triton X-100. Bound antibody is detected by the addition of $^{125}$I-protein A.

Since none of the coccidial polypeptides, described above, which confer immunity, are capable of being purified to homogeneity by known separation or purification methods it has been impossible to characterize the amino acid composition of the individual polypeptides. Consequently, the antibodies directed against the various Eimeria antigens are used to identify, by immunological methods, protective coccidial immunogenic polypeptides produced by recombinant DNA technology. Recombinant DNA technology is defined herein as technology which allows segments of genetic information, DNA, from different cells, usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated from sporulating oocysts or sporozoites, incorporated into an appropriate cloning vector, transduced into an appropriate host cell and products of the host cell screened for the production of polypeptides which bind to the anti-*E. tenella* antibodies. The identified genes expressing the immunoreactive polypeptides are incorporated into an appropriate expression vector and expressed in an appropriate host cell system.

Cloning vector as used herein is defined as a DNA sequence which allows the incorporation of specific experimental foreign DNA, with the combined DNA being introduced into a host cell that can exist in a stable manner and express the protein dictated by the experimental DNA. The foreign DNA combined with the vector DNA constitutes a recombinant DNA molecule which is derived from recombinant technology. Cloning vectors may include plasmids, bacteriophage, viruses and cosmids. It is to be understood that any cloning vector may be used to clone the novel Eimeria immunogen DNA sequences, with the lambda gt11 being preferred. Host cells for cloning, DNA processing and initial expression generally include bacteria. The preferred cloning host is *Escherichia coli.* Expression vectors are defined herein as DNA sequences that are required for the transcription of cloned copies of genes and the translation of their mRNAs in an appropriate host. Such vectors can be used to express either procaryotic or eucaryotic genes in a variety of hosts such as bacteria, blue green algae, yeast cells, insect cells and animal cells. The immunogens may also be expressed in a number of virus systems. Specifically designed vectors allow the shuttling of DNA between bacteria-yeast or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The unique immunogenic proteins of the present invention may exist as, but are not limited to, the complete proteins specified by the defined gene in Eimeria, native protein or as any fragment or subunit thereof, or as hybrids of the complete protein or its fragments or subunits. The complete protein, as used herein, refers to the full length polypeptide produced by the appropriate Eimeria gene. The complete protein may be obtained by purification from the appropriate species of Eimeria, or by expression in an appropriate expression vector of the corresponding recombinant derived gene product. Protein fragments or subunits refers to any portion of the protein which contains fewer amino acids than the complete protein and retains the ability to induce anticoccidial immunity. Hybrid proteins include, but are not limited to, fusion proteins or proteins resulting from the expression of multiple genes within the expression vector. A fusion protein is defined as one in which a limited number of amino acids coded for by the expression vector are expressed and the expression results in their attachment to the specific immunogenic polypeptide. Proteins resulting from multiple genes may include the specific immunogenic polypeptide linked to a second polypeptide or peptides by peptide bonds that enhance immune reactivity. The enhancing polypeptide portion may have the capability of increasing the immune response to the coccidial immunogen.

The appropriate coccidial DNA is isolated and identified by reacting the gene derived protein with anti-Fraction V and anti sporozoite antibodies. Recombinant coccidial polypeptides are produced by cloning the natural gene from either genomic DNA or cDNA. Genomic DNA, a preferred method of obtaining specific genes, is extracted from sporocysts or sporozoites by disrupting the parasites, about $1.5\times 10^8$, by treatment with about 0.5% SDS and about 15 mM EDTA. The released DNA is solubilized by digestion with a proteolytic enzyme, preferably Proteinase K, about 100 $\mu$g/ml at about 50° C. for about 3 hours. Genomic DNA is purified by about two extractions with phenol, about two extractions with a mixture of phenol, chloroform and isoamyl alcohol (about 25:24:1), about two extractions with chloroform and isoamyl alcohol (about 24:1) and about two successive precipitations with sodium acetate/ethanol. The DNA is washed twice with about 70% ethanol and resuspended in Tris-HCl, about 10 mM and EDTA, about 1 mM (TE) at the approximate concentration of about $5\times 108$ parasite equivalents per ml. Any associated RNA is selectively removed by digestion with RNase, preferably heat inactivated RNase A, at a concentration of about 50 $\mu$g/ml for about 60 minutes at about 37° C. The RNase A and any other residual proteins are removed by a secondary digestion with Proteinase K in about 0.5% SDS/15 mM EDTA for about 3 hours at about 50° C. The genomic DNA is then extracted with organic solvents, precipitated with ethanol and washed with about 70% ethanol and collected by centrifugation. The genomic DNA pellet is suspended in TE at a concentration of about $2\text{-}3\times 10^9$ sporozoite equivalents/ml and quantitated by absorbance at 260 nm. Coccidial DNA is prepared for cloning by either physical, Old and Primrose, Principles of Gene Manipulation, 2nd Ed. University of California Press, p. 20 (1981) or chemical, Smithies et al., Science 202:1284–1289 (1978), fragmentation of high molecular weight DNA The genomic DNA is then incorporated into an appropriate cloning vector, see cloning vectors for cDNA below. The cloning vectors are transduced into a host cell and screened by a procedure similar to that of Huynh et al., In "DNA cloning: A practical approach", Vol. I, Glover Ed., IRL Press Oxford, pp. 49–78 (1985). Positive clones are transferred to expression vectors engineered for high volume production of the desired immunogenic protein. The expression vectors, see below, are transformed into suitable host cells, see below, for the production of immunogenic protein.

The most preferred process for obtaining genetic information for the production of coccidial immogenic polypeptides is the isolation of mRNA coding for a specific protein. Total RNA is isolated from oocysts, sporulated for about seven hours, and sporozoites using the quanidinium thiocyanate method of Chirgwin et al., Biochem. 18:5294–5299 (1979). Polyadenylated RNA is selected by oligo (dT) cellulose chromatography, Aviv and Leder, Proc. Nat. Acad. Sci. USA 69:1408–1412 (1972). Utilizing the polyadenylated RNA, about 6 to about 9 $\mu$g, first and second-strand cDNA reactions are performed using a reverse transcriptase such as AMV-reverse transcriptase, a RNase such as RNase H and a DNA polymerase such as DNA polymerase I following the procedure described by Gubler and Hoffman, Gene 25:263–269 (1983). The cDNA is methylated with a methylase such as Eco RI methylase, blunt ended with a polymerase such as T4 DNA polymerase and ligated to phosphorylated oligo nucleotide linkers such as Eco RI dexanucleotide linkers with a DNA ligase such as T4 DNA ligase. The linker ligated cDNAs are digested to completion with a restriction enzyme such as EcoR1 and the digested linkers removed by repeated precipitations with absolute ethanol out of 2M NH$_4$ acetate, Okayama and Berg, Mol. Cell. Biol. 2:161–170 (1982). The cDNA was further purified on an Elutip-d column (Schleicher & Schell). Restriction enzymes or restriction endonucleases are enzymes that recognize specific nucleotide base sequences within double stranded DNA and cleave the two strands at a specific location within the recognition sequence. The purified cDNA, about 100 ng to about 500 ng, with 300 ng being preferred, is ligated into about 7.5 μg of commercially purchased, EcoRI-digested, alkaline phosphotase treated λgt11 vector DNA and packaged in vitro with commercially available packaging extracts according to the manufacturer's instructions (Amersham). Other acceptable vectors can be used, but λgt11 is preferred because it allows the inducible expression of Eimeria antigens in *E. coli* as β-galactosidase fusion proteins. Aliquotes of the packaged phage are transduced into *Escherichia coli* host strain Y1088 and these are plated on Luria-Bertani (LB) medium agar plates using about 2.5 ml LB soft agar containing about 600 μg/ml X-gal (5-bromo-4-chloro-3-indolyl-β-D-galactopyranoside) and about 16 mM isopropyl-β-D-thiogalactopyranoside (IPTG).

A cDNA library consisting of approximately $1 \times 10^7$ independant recombinant phage clones is generated. The nonrecombinant background, as determined by growth on X-gal/IPTG plates, is estimated to be about 13%.

Screening of the cDNA library is accomplished by the method of Huynh, et al. "In: DNA Cloning: A Practical Approach", Vol. I, Glover, Ed., IRL Press, Oxford, pp. 49–78 (1985). Packaged phage from the unamplified cDNA library were transduced into *E. coli* strain Y1090 as described by Huynh, supra, and plated at an appropriate density, about 0.5 to about $1.0 \times 10^5$ plaque forming units (pfu) per plate. The plates are incubated, at about 42° C. for about 3 hours, overlaid with nitrocellulose filters presoaked in about 10 mM IPTG, and reincubated overnight at about 37° C. The filters are removed, blocked with about 20% fetal calf serum in an acceptable buffer, such as Tris buffered saline (TBS) (about 50 mM Tris-HCl about 150 mM NaCl, at a pH of about 8.0) containing about 0.05% Tween 20 (TBST), and incubated with the appropriate antibody, generally rabbit anti sporozoite antibody or rabbit anti Fraction V antibody, diluted about 1:100 in TBST containing about 20% fetal calf serum for an appropriate length of time. All antisera are exhaustively preabsorbed with a concentrated lysate of lambda gt11 lysogen BNN93. Antibody binding sites are detected by contacting the filters with $^{125}$I-protein A. Positive plaques are picked, replated, and rescreened until each clone is shown to be plaque pure. An initial screen of the sporulated oocyst library of about $1 \times 10^6$ independent recombinants with rabbit anti sporozoite antibody results in the isolation of about 57 antigen expressing phage. Secondary and tertiary rescreening reveals that greater than 29% of the clones initially identified remain positive.

Cross screening involves the spotting of about 1 μl of phage lysate from each plaque purified clone on a lawn of *E. coli* Y1090 cells with recombinant fusion proteins being induced as previously described. The proteins are transferred to nitrocellulose and immunoblotted as described above. The cross screening antisera include rabbit anti-*E. tenella* unsporulated oocyst antibody, rabbit anti-*E. tenella* sporozoite antibody, rabbit anti Fraction V and rabbit anti-*E. tenella* schizont antibody. All antisera are exhaustively preabsorbed with a concentrated lysate of λgt11 lysogen BNN93.

Recombinant and wild type λgt11 phage are introduced as lysogens into *E. coli* host strain Y1089 at a multiplicity of about 10. Lysogenized clones are grown in about 10 ml of Luria Bertani (LB) medium supplemented with about 50 μg/ml ampicillin at about 32° until an optical density at 600 nm of 0.25 is reached. Phage replication is induced by a temperature shift to about 45° C. for about 20 minutes and the synthesis of β-galactosidase fusion proteins is induced by the addition of about 10 mM IPTG to the culture medium. The cells are incubated and collected by centrifugation and the pellets are resuspended in about 250 μl of NET buffer, about 50 mM Tris-HCl, pH about 7.5, about 150 mM NaCl, about 5 mM ethylenediaminetetraacetic acid (EDTA), with about 2% SDS. The cells are lysed by boiling and the bacterial DNA is removed by centrifugation. The supernatant fluids are analyzed on about 5% SDS-PAGE under denaturing conditions. Duplicate gels are run with one being stained with silver stain (Biorad) and the other immunoblotted by the method of Towbin et al., Proc. Natl. Acad. Sci. USA 76:4350–4354 (1979).

Monospecific antibodies to each of the recombinant immunogens are affinity purified from polyspecific antisera by a modification of the method of Hall et al., Nature 311:379–382 (1984), prepared by immunizing rabbits as described above with purified recombinant *E. tenella* proteins as described below or prepared as monoclonal antibodies using the technique of Kohler and Milstein, Nature 256:495–497 (1975). Monospecific antibody as used herein is defined as a single antibody species or multiple antibody species with homogenous binding characteristics for the relevant antigen. Homogenous binding as used herein refers to the ability of the antibody species to bind to a specific antigen or epitope, such as those associated with the specific native or recombinant *E. tenella* group immunogens. The Hall technique of preparing monospecific antibodies from polyclonal antiserum requires the preparation of filter plaque lifts from purified recombinant clones as is done for screening. Approximately $2 \times 10^5$ plaque forming units are plated to give close to semiconfluent lysis at the end of the 37° C. incubation period. The nitro-cellulose is removed from the plates and is blocked with about 20% fetal calf serum in TBST for about 4 hours and incubated overnight with about 20 ml of the preabsorbed polyspecific serum, diluted about 1:200 with about 20% fetal calf serum in TBST containing about 0.02% NaN$_3$. The filters are washed at least 5 times with about 50 ml TBST for at least 20 minutes and 1 time with about 0.15 mM NaCl and about 0.05% Tween 20. The antibodies are eluted with an acceptable eluant, such as about 0.2M glycine-HCl, about 0.15M NaCl and about 0.05% Tween 20, at a pH of about 2.8 for about 30 minutes. The pH is adjusted to about 8.0 and the antibodies are stored.

Monoclonal antibody reactive against each of the recombinant *E. tenella* group immunogens, antigens or epitopes is prepared by immunizing inbred mice, preferably Balb/c with the appropriate recombinant protein. The mice are immunized intraperitoneally with about 100 ng to about 10 μg, preferably about 1 μg recombinant immunogen per 0.5 ml in an equal volume of an acceptable adjuvant. Such acceptable adjuvants include, but are not limited to, Freund's complete, Freund's incomplete, alum-precipitate, water-in-oil emulsion containing *Corynebacterium parvum* and tRNA. The mice are given intravenous booster immunizations of an equal amount of recombinant immunogen without adjuvant at about days 14, 21, and 63 post primary immunization. At about day three after the final booster immunization individual mice are serologically tested for anti-recombinant immunogen antibody. Spleen cells from antibody producing mice are isolated and fused with murine myeloma cells, such as SP-2/0 or the like, by techniques known to the art, see Kohler and Milstein, Nature 256: 495-497 (1975). Hybridoma cells are selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson, Soft Agar Techniques, in Tissue Culture Methods and Applications, Kruse and Paterson, Eds. Academic Press, p. 276 (1973). Discrete colonies are transfered into individual wells of culture plates for cultivation in an appropriate culture medium. Antibody producing cells are identified by screening with the appropriate *E. tenella* recombinant immunogen. Immunogen positive hybridoma cells are maintained by techniques known in the art. Specific anti-recombinant *E. tenella* monoclonal antibodies are produced by cultivating the hybridomas in vitro or preparing ascites fluid in mice following hybridoma injection by procedures known in the art.

The parasite antigens are assayed by Western Blot analysis as described above. The clones of interest may be placed into four antigenic groups, according to the reaction of the expressed polypeptides with the above described antisera, see Table 1. Different clones of the same group express portions of the same polypeptide, as judged by antibody reactivity, DNA crosshybridization, and restriction endonuclease mapping, see below.

one-tenth volume of a 3M (pH 5.6) stock solution, precipitated with ethanol, chilled and collected by centrifugation. After suspending the pellet in TE, the DNA is electrophoresed in agarose containing ethidium bromide to resolve the insert from the phage arms.

Fractionation of the inserts is verified by visualization under ultraviolet light. The inserts are electrophoresed onto NA-45 (Schleicher & Schuell) membranes and then eluted from the membranes. Insoluble particles are removed by centrifugation and the soluble material is extracted with phenol, phenol/chloroform/isoamyl alcohol and chloroform/isoamyl alcohol. The DNA is precipitated with sodium acetate/ethanol, washed with ethanol and air dried. An aliquot of each DNA is analyzed on an analytical agarose gel for confirmation.

Expression of the genes coding for the protective coccidial immunogens is accomplished in a number of different host cells with a variety of promoter-expression systems. The host cells include bacteria, yeast, insect, and mammalian cells. The antigens may also be expressed in a number of virus systems. Although the genes can be expressed in numerous procaryotic cells and various eucaryotic cells the most preferred host cell is *Escherichia coli*. The expression vectors which can be used for the expression of the protective immunogens include, but are not limited to, pBR322, pPLa2311, pKC30, ptac12, λgt11, pAS1, pLC24, pSB226, pRIT2T and SV40 with a CheY-pUC derived vector designated pJC264 being preferred. It is desired and intended that there be included in this invention, the use of *Eimeria tenella* immunogens, which are native proteins or fragments thereof, recombinant proteins or fragments thereof, or fusion proteins linked to other proteins which may or may not enhance the Eimeria peptides immunogenicity. The fusion immunogens may be designed in such a manner that the immunogenic expression protein contains an additional polypeptide portion encoded for by the expression plasmid or an additional peptide portion that has been added to the gene by the inclusion of an additional DNA base sequence. The

TABLE 1

| | IMMUNE REACTIVITY OF ISOLATED CLONE PRODUCTS | | | | |
|---|---|---|---|---|---|
| CLONE | ANTI FRACTION V | ANTI-E.t. UNSPORULATED OOCYST | ANTI-E.t. SPOROZOITE | ANTI-E.t. SCHIZONT | ANTI-E.a. SPOROZOITE |
| A | + | + | + | − | + |
| B | + | − | + | − | + |
| C | + | − | + | − | − |
| H | + | − | + | n.d. | − |
| F | + | n.d. | n.d. | n.d. | n.d. |

E.t. denotes *Eimeria tenella* while E.a. denotes *Eimeria acervulina*. A (+) denotes that the antibody can react with the specific recombinant derived protein while a (−) denotes a lack of such a response and n.d. means not done.

Purification of the cDNA inserts from λgt11 clones is accomplished by cutting the recombinant phage DNA to completion with EcoRI, about five fold enzyme excess, in a reaction buffer composed of about 50 mM NaCl/about 100 mM Tris-HCl, about pH 7.5, about 5 mM MgCl$_2$. The reaction products are adjusted to about 0.3M sodium acetate by the addition of about pJC264 plasmid is designed to include the expression of an 88 amino acid portion of the *E. coli* CheY protein operably attached to 5 linker amino acids linked or fused to the various Eimeria tenella peptides. Operably attached refers to an appropriate sequential arrangement of nucleotide segments, linkers, or genes such that the desired protein will be produced by cells containing an expression vector containing the operably attached genes, segments or linkers. The nucleotide sequence of the CheY gene and the amino acid sequence produced from the gene are shown in the following table.

TABLE 2

Amino Acid and Nucleotide Sequences
of the CheY Protein 10      20      30      40      50
*       *       *       *       *

TABLE 2-continued
Amino Acid and Nucleotide Sequences of the CheY Protein

| ATG GCG GAT | AAA GAA CTT | AAA TTT TTG | GTT GTG GAT | GAC TTT TCC | ACC ATG CGA |
|---|---|---|---|---|---|
| MET ALA ASP | LYS GLU LEU | LYS PHE LEU | VAL VAL ASP | ASP PHE SER | THR MET ARG |
|  |  |  | 10 |  |  |
| 60 | 70 | 80 | 90 | 100 |  |
| CGC ATA GTG | CGT AAC CTG | CTG AAA GAG | CTG GGA TTC | AAT AAT GTT | GAG GAA GCG |
| ARG ILE VAL | ARG ASN LEU | LEU LYS GLU | LEU GLY PHE | ASN ASN VAL | GLU GLU ALA |
| 20 |  |  | 30 |  |  |
| 110 | 120 | 130 | 140 | 150 | 160 |
| GAA GAT GGC | GTC GAC GCT | CTC AAT AAG | TTG CAG GCA | GGC GGT TAT | GGA TTT GTT |
| GLU ASP GLY | VAL ASP ALA | LEU ASN LYS | LEU GLN ALA | GLY GLY TYR | GLY PHE VAL |
|  | 40 |  |  | 50 |  |
| 170 | 180 |  | 190 | 200 | 210 |
| ATC TCC GAC | TGG AAC ATG | CCC AAC ATG | GAT GGC CTG | GAA TTG CTG | AAA ACA ATT |
| ILE SER ASP | TRP ASN MET | PRO ASN MET | ASP GLY LEU | GLU LEU LEU | LYS THR ILE |
|  | 60 |  |  |  | 70 |
| 220 | 230 | 240 | 250 | 260 |  |
| CGT GCG GAT | GGC GCG ATG | TCG GCA TTG | CCA GTG TTA | ATG GTG ACT | GCA |
| ARG ALA ASP | GLY ALA MET | SER ALA LEU | PRO VAL LEU | MET VAL THR | ALA |
|  |  | 80 |  |  |  |

Linker amino acids are defined herein as those amino acids used to link an *E. tenella* defined gene, one which produces a native protein, to a fusion protein. Any amino acid or group of amino acids may be used as linkers, however, the preferred amino acid sequence and nucleotide sequence of the peptide linking the CheY protein to the *E. tenella* protein is:

```
5' GCC CAA GAA TTC GGN 3'
   ALA GLN GLU PHE GLY
```

The 3' terminal N constitutes the first nucleotide of the cDNA and may represent any nucleotide with the resultant amino acid always being glycine.

The preferred plasmid pJC264 is derived from the plasmid pJC220 which is in turn derived from a construct containing a portion of the *E. coli* chemotaxis gene, CheY, and the gene for rat atrial natriuretic factor (ANF). The CheY-ANF plasmid is constructed from the pLC1-28, Col E1-derived plasmid described in Matsumura et al. J. Bacteriol 160:36-41 (1984). The Che operon fragment containing the 3' portion of the Che B gene and the CheY and CheZ genes is excised from the pLC1-28 plasmid as a BamHI-HindIII fragment and subcloned into a BamHI HindIII digested pUC13 plasmid (PL Biochemicals) to give a pUC13-CheY-CheZ plasmid. *Escherichia coli* JM105 clones transformed by pUC13-CheY-CheZ express CheY and CheZ polypeptides off the lac promoter contributed by the pUC13 vector, Davis et al., Basic Methods In Molecular Biology, Elsevier, New York, New York, pg. 30 (1986). The pUC13-CheY-CheZ plasmid is digested at the unique PstI site internal to the CheY coding region, see Matsumura et al., supra, and at the unique SmaI site in the pUC13 polylinker 3' to the inserted Che DNA. The resulting 3 kb PstI-SmaI fragment containing the pUC13 vector the 3' portion of the Che B gene and the DNA encoding the N-term 100 residues of CheY was recombined with the 160 bp PstI-HindIII fragment of pSCN1-(rat ANF-26) that encodes the Met-(rat-ANF-26) sequence and contains 50 bp of untranslated RAS1 sequence 3' to the termination codon for the ANF peptide. This expression vector is termed the CheY-ANF vector. The pSCN1-(rat-ANF-26) fusion plasmid is constructed from the pSCN1 plasmid which expresses the N-terminal 165 amino acids of the yeast RAS1 protein SC1N, Temeles et al., Nature 313: 700-703 (1985). Plasmid pSC1N is digested to completion with AccI, and the ends are filled in with *E. coli* DNA polymerase I large fragment (Klenow polymerase). A synthetic ANF gene is ligated to pSC1N and used to transform competent *E. coli* JM105 cells. The nucleotide sequence of the CheY-ANF plasmid from the EcoRI restriction site to the first HindIII restriction site prior to the CheY fragment is identical to that shown for pUC19 by Yanisch-Perron et al., Gene 33: 103-119 (1985).

Figure 7:
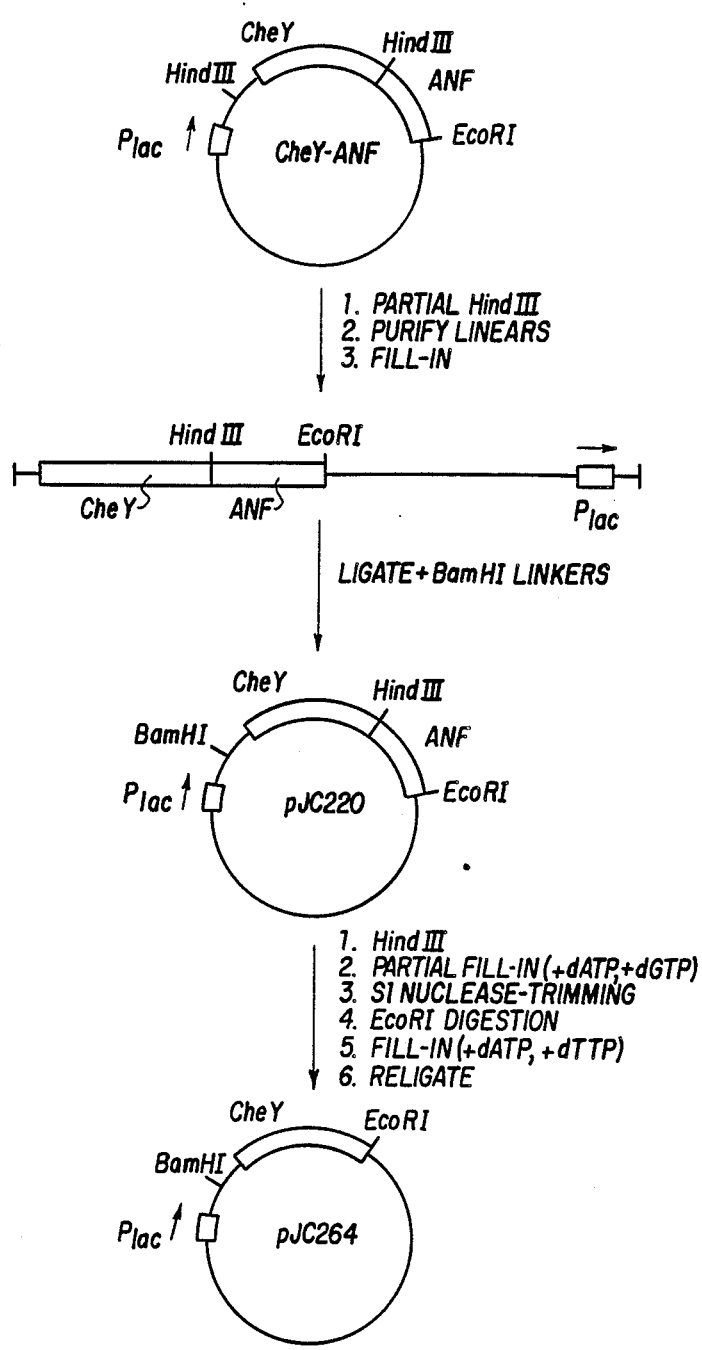
FIG. 7 illustrates the conversion of the CheY-ANF plasmid to the pJC264 plasmid.
Figure 8:
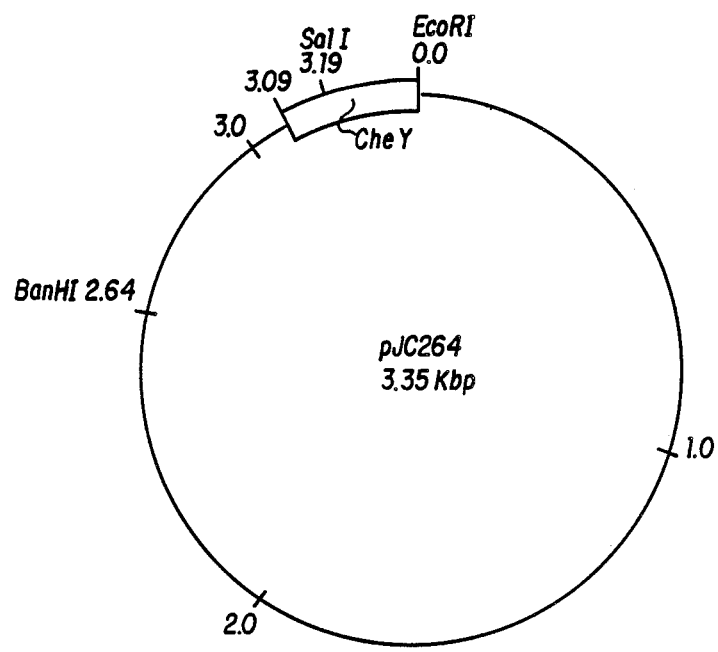
FIG. 8 is a restriction map of the pJC264 plasmid.

The pJC264 expression plasmid contains a unique EcoRI site, in the same reading frame as the lambda gt11 EcoRI site, which permits easy subcloning and expression of EcoRI fragments from lambda gt11 expression libraries. The inclusion of a portion of the CheY gene product in the resulting fusion protein may facilitate stabilization of the protein and enhance the purification of the protein. The small size of the CheY protein compared with other fusion carriers such as β-galatosidase, permits a more favorable molar yield of the protein of interest for a given mass of fusion protein. The CheY containing plasmid pJC264 results in high expression levels of fusion proteins with the first 93 amino acids of the amino terminus being derived from the *E. coli* CheY protein and linkers. As noted above the pJC264 plasmid is derived from the CheY-ANF plasmid as shown in FIG. 7. CheY-ANF is partially digested with HindIII and electrophoresed in about 0.7% Seaplaque agarose gel. Full-length linear DNA is mechanically excised, removed from the gel by melting, purified on a NACS column (BRL) and recovered by ethanol precipitation. The DNA fragment is made blunt by filling in the HindIII ends with the Klenow fragment of DNA Polymerase I (Boehringer Mannheim), phenol-extracted and ethanol precipitated. BamHI linkers phosphorylated at the 5' position are ligated to the purified DNA, and *E. coli* HB 101 is transformed directly with the ligation mix. Ampicillin resistant transformant colonies are restriction-mapped for the BamHI linker. A colony designated pJC220 contains the BamHI linker in place of the promoter-proximal HindIII site. The plasmid now has a HindIII site at the 3' end of the CheY coding region and is therefore unique. Plasmid pJC220 is digested with HindIII and two bases of the four base overhang are filled in with the Klenow fragment of DNA Polymerase I in the presence of dATP and dGTP. The remaining two bases of the overhang are removed with S1 nuclease, leaving a blunt end. The DNA is then digested with EcoRI and filled in with the Klenow fragment of DNA Polymerase I in the presence of dATP and dTTP. The plasmid is recircularized by blunt end ligation with T4 DNA ligase to yield pJC264, which contains a unique EcoRI site at the 3' end of the CheY coding region. The new EcoRI site is in the same reading frame as the EcoRI site of lambda gt11, permitting direct subcloning and expression, as CheY fusion proteins, of antigens identified by expression in lambda gt11 libraries. The pJC264 restriction map is shown in FIG. 8.

Minipreps of recombinant λgt11 bacteria phage are prepared and phage DNA is isolated. The gene insert for each antigen is removed by EcoRI digestion and fractionated from the phage arms by agarose gel electrophoresis. The genes are then inserted into the plasmid pJC264 which has been linearized at its unique EcoRI site and phosphatased to decrease the efficiency of autoligation. Ligation products are then transfected into the bacterial host, *E. coli* JM83 using standard CaCl$_2$ methods known in the art and the transformants are selected on ampicillin plates. Ampicillin resistant colonies are grown on an analytical scale to score for the presence of an insert, score for orientation of the foreign DNA with respect to the bacterial promoter and score for expression of bacterial fusion proteins by Western blot analysis, using polyclonal antisera raised against *E. tenella* immunogens.

DNA inserts are isolated from phage clones representative of the various immunogen groups identified above and are also sub cloned into the puc18 plasmid vector as described above for the CheY vector, pJC264. Restriction endonuclease maps of members of each group are prepared. The restriction endonucleases included, but are not limited to, the following:

| | | |
|---|---|---|
| AluI | HindIII | SalI |
| ApaI | HincII | Sau3a |
| AvaI | HinfI | SstI |
| AvaII | HpaII | SstII |
| BamHI | KpnI | TaqI |
| BglI | NcoI | XbaI |
| ClaI | PstI | XhoI |
| HaeIII | PvuI | XhoII |
| HhaI | PvuII | | all of which are available commercially. The following table contains the groups, clone designation within each group and the restriction endonucleases which are unable to cut within the clone insert.

TABLE 3

RESTRICTION ENDONUCLEASE SITES ABSENT FROM DESIGNATED CLONES

| Group | Clone Designation | Restriction Endonucleases |
|---|---|---|
| A | SO6' | BamHI, HindIII, KpnI, NcoI, |
| | SP1 | AvaI, ClaI, XhoI, SalI, |
| | SO67 | SstI, SstII, XbaI, BqlI, |
| B | SO9 | BamHI, HincII, KpnI, |
| | SO24 | NcoI, ClaI, SalI, SstI, |
| | SO7' | XbaI |
| | SO1' | |
| C | SP54 | BamHI, KpnI, HincII, |

TABLE 3-continued

RESTRICTION ENDONUCLEASE SITES ABSENT FROM DESIGNATED CLONES

| Group | Clone Designation | Restriction Endonucleases |
|---|---|---|
| | SP59 | NcoI, ClaI, PvuII, XhoI, SalI, SstI, SstII, XbaI, BglI |
| H | SO311 | BamHI, HindIII, KpnI, |
| | SO227 | AvaII, ApaI, NcoI, |
| | SO231 | AvaI, ClaI, PstI, XhoI, SalI, SstII, XbaI |
| F | SO216 | ApaI, AvaI, AvaII, BamHI, BglI, ClaI, HincII, NcoI, PstI, PvuII, SalI, SstI, SstII, XbaI, XhoI |

Some restriction endonucleases are capable of cleaving one or more clones within a group but not all clones. In the B group, additional restriction endonucleases which cleave at least one of the four clones include AvaI, PstI, SstII. These sites have not been mapped. In the H group, the restriction endonuclease SstI does cleave within all three of the clones, but the site has not yet been mapped.

The above information is determined by growing the pUC 18 recombinant plasmids as mini-preparations in LB broth and isolating the DNA using the alkaline lysis method described below. The DNA is resuspended in digestion buffer such as TE buffer which contains, about 10 mM Tris-HCl (about pH 8.0), about 1 mM EDTA (about pH 8.0), containing DNase-free pancreatic RNase, about 20 μg/ml and mixed on a Vortex mixer briefly. The DNA samples are then digested with a variety of restriction endonucleases (available from Bethesda Research Laboratories) to determine which had the ability to cleave the cDNA inserts. A mapping analysis is conducted by doing single and double digests of the insert/plasmid. DNA fragments are separated electrophoretically on about 1% agarose gels, and sized by comparison to DNA markers which are run simultaneously on the same gels. Maps are constructed of each clone by entering the fragment size data and known vector restriction sites into the Intelligenetics Restriction Map Generator program (MAP, Intelligenetics, Inc.). The derived location along the nucleotide sequence of the enzymatic cleavage sites is accurate to about the ±10% level. The restriction map of the group A clones are shown in FIG. 1. The SO6 gene is about 1886 nucleotides (nt) in length with restriction sites at the following base locations: 118 (ApaI), 284 (PstI), 293 (PvuII), 597 (PstI), 1283 (PstI), 1820 (HincII) and 1837 (AvaII). The SPI gene is about 1404 nt with restriction sites at the following base locations: 213 (PstI), 889 (PstI), 1386 (HincII) and 1398 (AvaII). The SO67 gene is 822 nt in length with restriction sites at the following base locations: 108 (PstI), and 816 (HincII).

Figure 2:
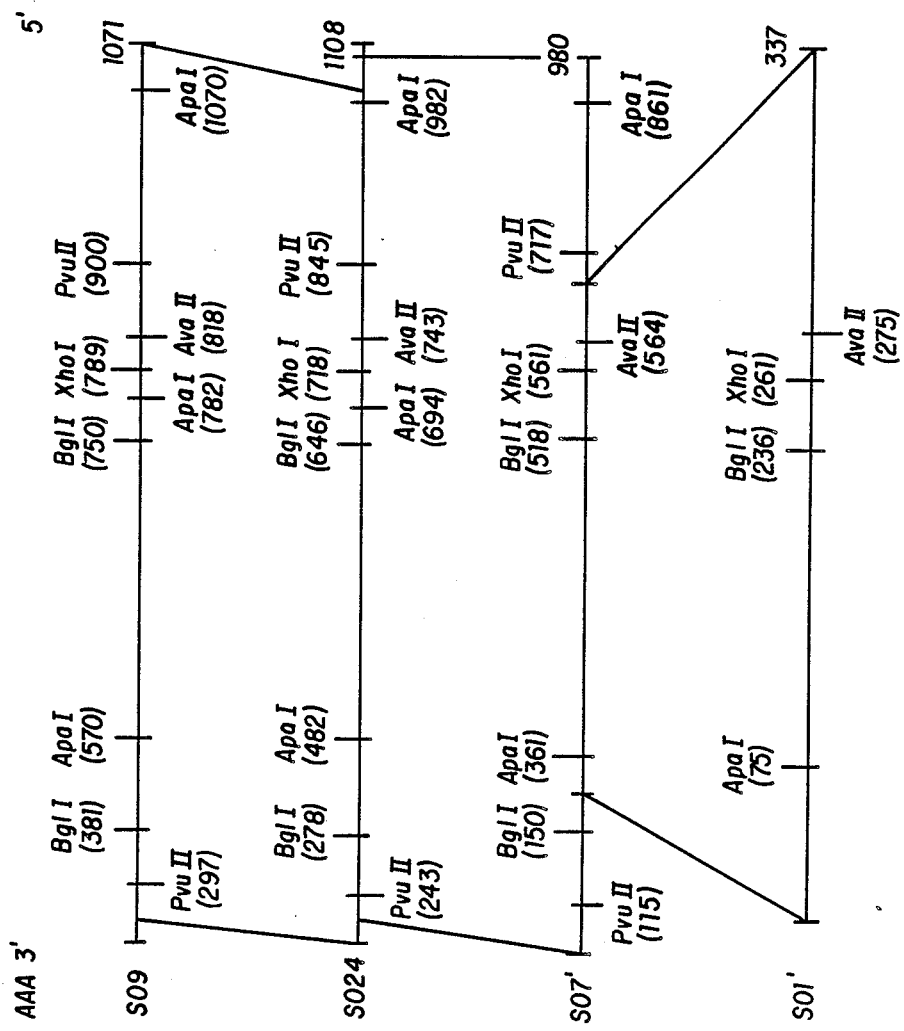
FIG. 2 is a restriction map of group B 23 clones.

The restriction maps of the group B clones are shown in FIG. 2. The SO9 gene is about 1071 nt in length with restriction sites at the following base locations: 297 (PuvII), 381 (BglI), 570 (ApaI), 750 (BglI), 789 (XhoI) and 900 (PvuII). The SO24 gene is about 1108 nt in length with restriction sites at the following base locations: 243 (PvuII), 278 (BglI), 482 (ApaI), 646 (BglI), 694 (ApaI), 718 (XhoI), 743 (AvaII), 845 (PvuII) and 982 (ApaI). The SO7 gene is about 980 nt in length with restriction sites at the following base locations: 115 (PvuII), 150 (BglI), 361 (ApaI), 518 (BglI), 561 (XhoI), 564 (AvaII), 717 (PvuII) and 861 (ApaI). The SOI gene is about 337 nt in length with restriction sites at the following base locations: 75 (ApaI), 236 (BglI), 261 (XhoI) and 275 (AvaII).

Figure 3:
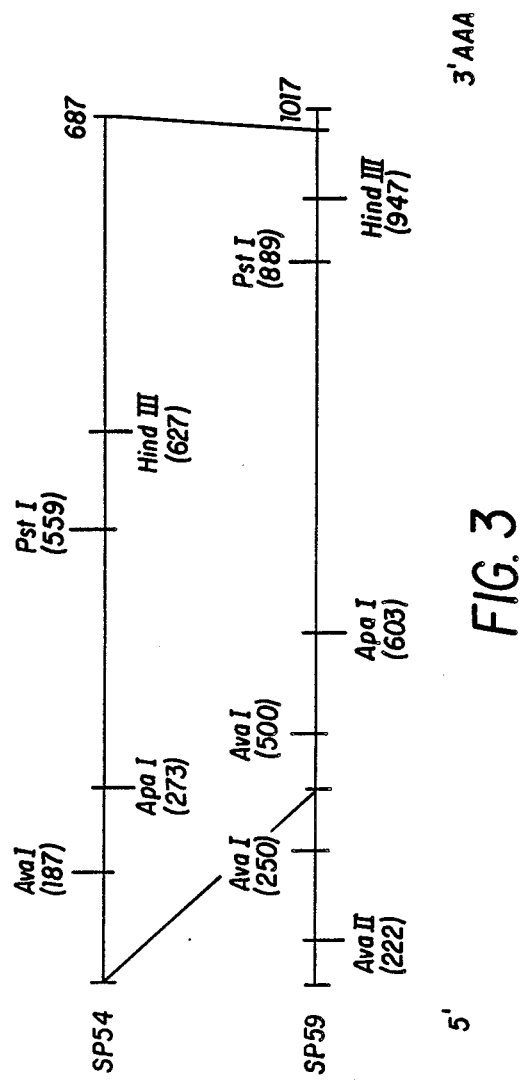
FIG. 3 is a restriction map of group C 25 clones.

The restriction maps of the group C clones are shown in FIG. 3. The SP54 gene is about 687 nt in length with restriction sites at the following base locations: 187 (AvaI), 273 (ApaI), 559 (PstI) and 627 (HindIII). The SP59 gene is about 1017 nt in length with restriction sites at the following base locations: 222 (AvaII), 250 (AvaI), 500 (AvaI), 603 (ApaI), 682 (ApaI), 889 (PstI) and 947 (HindIII).

Figure 4:
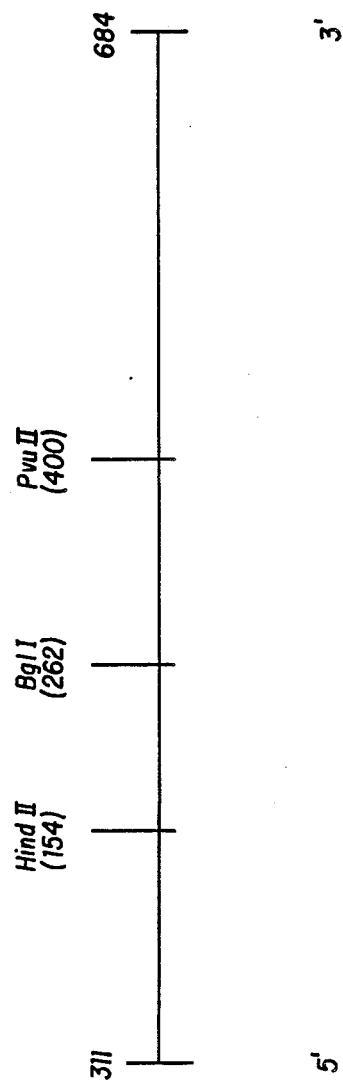
FIG. 4 is a restriction map of group H 27 clones.

The restriction map of a group H clone is shown in FIG. 4. The SO311 gene is about 684 nt in length with restriction sites at the following base locations: 154 (HincII), 262 (BglI) and 400 (PvuII). The SO227 gene is 631 nt in length with restriction sites at the following base locations: 257 (HincII), 369 (BglI) and 537 (PvuII). The SO231 gene is 632 nt in length with restriction sites at the following base locations: 255 (HincII), 382 (BglI) and 514 (PvuII).

Figure 5:
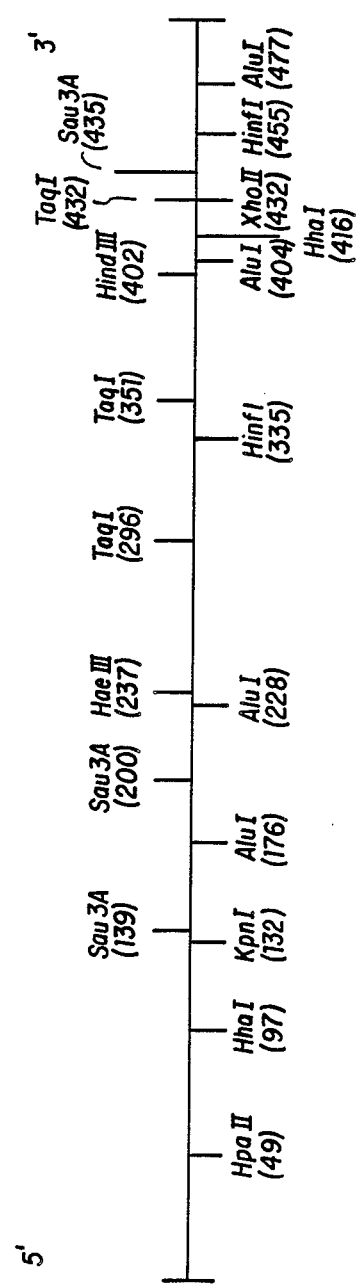
FIG. 5 is a restriction map of group F 29 clones.

The restriction map of a Group F clone is shown in FIG. 5. The SO216 gene is about 487 nt in length with restriction sites at the following base locations: 49 (HpaII), 97 (HhaI), 132 (KpnI), 139 (Sau3A), 176 (AluI), 200 (Sau3A), 228 (AluI), 237 (HaeIII), 296 (TaqI), 335 (HinfI), 341 (TaqI), 402 (HindIII), 404 (AluI), 415 (HhaI), 432 (TaqI), 435 (XhoII), 435 (Sau3A), 455 (HinfI) and 477 (AluI). The first eight nts and the last eight nts represent the linker nts and are not part of the E. tenella Group F gene.

Production of recombinant immunogenic coccidial proteins, recombinant fusion proteins and recombinant CheY fusion proteins, with recombinant CheY fusion proteins being preferred, is accomplished by overnight culturing, in 2×YT medium containing ampicillin, of selected recombinant bacteria isolated from a single colony The overnight culture is used to inoculate about 500 ml of 2×YT plus ampicillin. The culture is grown at about 37° C. with aeration until the mid-logarithmic phase of growth is reached, at which time IPTG is added to a final concentration of about 100 μM. The cells are incubated for about another 3 to 4 hours, chilled on ice and collected by centrifugation. The cells are washed, collected by centrifugation and resuspended in about 10 ml of Buffer A which consists of about 30 mM Tris-HCl, about pH 8.0, about 5.0 mM EDTA and about 1 mm phenylmethylsulfonylfluoride. The cell suspension is sonicated while maintained in an ice bath in three minute bursts using a Branson cell disrupter Model 350. The sonicate is clarified by centrifugation at about 27,000×g for about 45 minutes at about 4° C. This constitutes the first supernatant fluid. The pellet (P1) is washed in about 10 ml of buffer A containing 0.1% w/v Triton X-100 for about 30 minutes in an ice-bath and recentrifuged. The supernatant fluid is collected and designated the second supernatant. The pellet (P2) is washed twice in the same buffer, buffer A. The washes are discarded. The washed pellet, P2 is then resuspended in about 1.0 ml of about 6M guanidine-HCl containing about 100 mg dithiothreitol and the suspension incubated at about 50° C. (for about 2 hours). The suspension is diluted to 10 ml with about 7M urea and is clarified by centrifugation at about 27,000×g for about 45 minutes at about 4° C. with the supernatant fluid constituting the third supernatant. Due to differences in solubility of the various fusion proteins, some are found in the first supernatant, some in the second supernatant and some are found in the third supernatant. For example, a representative clone protein from immunogen group A, SO6-CheY, was found in the first, second and third supernatants. Representative proteins from clones of group B (SO7), C (SP54), H (SO311) and F (SO216) were found in the third supernatant. Both the SO7-CheY and SP54-CheY fusion proteins were unretarded by chromatography on hydroxyapatite. The SO311-CheY fusion protein bound to hydroxyapatite, and could be eluted with 160 mM phosphate buffer. The SO6-CheY fusion protein from the third supernatant fluid was further purified by Trisacryl M-DEAE chromatography.

Representative Eimeria immunogen clones are assayed to determine the nucleotide sequence of each specific gene by one or more of three standard techniques. In some cases the nucleotide sequence of the cDNAs is determined using the chemical degradation method of Maxam and Gilbert, Methods in Enzymology, 65 (part 1): 497–559 (1980). More routinely, the nucleotide sequence is determined by the dideoxy chain termination technique, using denatured plasmid templates (plasmid pUC18, containing assorted subsequences of the Eimeria cDNAs) as described by Hattori and Sakaki, Analyl. Biochem. 152:232–238 (1986). Finally, some nucleotide sequences are determined by subcloning the cDNA insert, or portions of it, into bacteriophage mp 18 and sequencing secreted single-stranded recombinant phage templates using the standard dideoxy chain-termination sequencing methodology of Messing, Methods in Enzymology 101:20–78 (1983). In addition to AMV reverse transcriptase and the Klenow fragment of DNA polymerase I, a modified T7 DNA polymerase has been employed, see Tabor and Richardson, Proc. Nat. Acad. Sci. U.S.A. 84:4767–4771 (1987).

The amino acid sequence is deduced from the determined nucleotide sequence by combining the following information. Each of the cDNAs in the phage expression vector λgtII was identified using polyclonal antisera when expressed as a fusion protein with β-galactosidase. The fusion junction between β-glactosidase and the immunogen consists of a Glu residue linking the carboxy-terminus of β-galactosidase with a Phe residue at the N-terminus of the immunogen (within the linker region). The EcoRI restriction enzyme cleaves between the first and second nucleotide of the Glu codon when reading from the 5' to 3'. This junction (and reading frame, cloning site), at the EcoRI cleavage site, is regenerated in each subsequent cloning event involving the entire cDNA irrespective of the subcloning vector, pUC18, mp18 or pJC264. Consequently, the reading frame can be unequivocally identified and the nucleotide sequence translated once the orientation of the insert in these three vectors is established. The orientation of the cDNA insert in plasmid, pUC18 and pJC264, or phage, mp18, vectors is accomplished by restriction enzyme mapping, known in the art. Once asymmetric restriction enzyme recognition sequences are identified within the cDNA insert, insert orientation and transcriptional orientation can be unequivocally assigned when the recognition sequences are similarly predicted by the nucleotide sequence. All amino acid sequences depicted herein read from the amino terminus to the carboxyl terminus.

Group A clone nucleotide sequences and the resulting Group A immunogen amino acid sequences are exemplified by the representative clone SO67. This clone is entirely contained within the SO6 clone. Of the approximately 870 nucleotides in this clone the first 162 nucleotides starting at the 5' end have been sequenced. The transcriptional orientation and therefore the correct reading frame can be deduced unambigiously based upon the location in the nucleotide sequence of restriction enzyme recognition sequences which are predicted by restriction enzyme mapping of the CheY-SO67 recombinant plasmid. The nucleotide sequence and the resulting 53 amino acid sequence is shown in Table 6. An additional 221 nucleotide sequence, see Table 7, has been obtained from the 3' end of the clone but the reading frame has not been deduced.

Group B clone nucleotide sequences and the resulting Group B immunogen amino acid sequences are exemplified by the representative clone SO7. All 957 nucleotides in this clone have been sequenced. The reading frame can be deduced unambiguously by correlating the position of restriction enzyme sites asymmetrically located within the cDNA with the location of their respective recognition sequences as predicted by the nucleotide sequence analysis. The nucleotide sequence and the amino acid sequence are shown in Table 8.

Group C clone nucleotide sequences and the resulting Group C immunogen amino acid sequences are exemplified by the representative clone SP54. This clone is entirely contained within the SP59 clone. Of the approximately 700 nucleotides in this clone the first 157 nucleotides starting at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping of the CheY-SP54 recombinant plasmid. The nucleotide sequence and the resulting 52 amino acid sequence is shown in Table 9.

Group H clone nucleotide sequences and the resulting Group H immunogen amino acid sequence are exemplified by the representative clone S0311. Of the approximately 650 nucleotides in this clone, the first 183 nucleotides at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping. The nucleotide sequence and the resulting 61 amino acid sequence is shown in Table 10. The last 283 nucleotides at the 3' end have been sequenced but the reading frame has not been deduced (see Table 11).

The molecular weights of the primary translation products encoded for by the cDNAs described above are determined by in vitro translation of the appropriate mRNA populations. In vitro translation of mRNA extracted from unsporulated oocysts, sporulating oocysts and sporzoites was performed using the rabbit reticulocyte cell free translation system, with either $^{35}$S-methionine or $^3$H-leucine as the incorporated indicator isotope. Specific in vitro translation products were immunoprecipitated using monospecific antibodies, as described in Example 6. The protocol for in vitro translation was as described in the technical bulletin from Promega Biotec (according to manufacturer's instructions) and for immunoprecipitation as in Taylor et al., Mol. Biochem. Parasitol. 10:305–318 (1983). The in vitro translation product immunoprecipitated by antibody specific for the Group A antigen, exemplified by clones SO6 and SO67 has a molecular weight of about 24 kiloDaltons (kD). The in vitro translation product immunoprecipitated by antibody specific for the Group B antigen, exemplified by clone SO7 has a molecular weight of about 28 kD while the minor immunogens have molecular weights of about 170, 24, 22, 16 and 12 kD. The additional minor specifically immunoprecipitable in vitro translation products are detectable when $^3$H-leucine is used as the labelled precursor amino acid. The 170 and 22 kD minor immunogens are also dectable with $^{35}$S-methionine. The major 28 kD immunogen is dectable only when $^3$H-leucine is used as the precursor amino acid. The in vitro translation product immunoprecipitaded by antibody specific for the Group C antigen, exemplified by clones SP54 and SP59 has not been determined. The in vitro translation product immunoprecipitaded by antibody specific for the Group H antigen, exemplified by clone SO311 has a molecular weight of about 28 kD while the minor immunogens have molecular weights of 48, 38, 33, 16, 13, 12 and 10 kD. The additional minor specifically immunoprecipitable in vitro translation products are detectable when 35S-methionine is used as the labelled precursor amino acid. The major 28 kD immunogen is detectable when both $^{35}$S-methionine and $^3$H-leucine are used.

The specific mRNAs extracted from sporulated oocysts and/or sporozoites of E. tenella were sized by Northern blot analysis according to the method of Maniatis et al., Molecular Cloning, A Laboratory Manual, Cold Spring Harbor Laboratory, Cold Spring Harbor, N.Y., pg. 202 (1982) and the method described in Transfer and Immoblization of Nucleic Acids to S & S Solid supports, published by Schleicher and Schuell, Inc., pgs. 16-19 (1987). The mRNA encoding the A immunogen, exemplified by clones SO6 and SO67, is 2.15+0.13 kilobases (kB) in length. The mRNA encoding the B immunogen, exemplified by clones SO7, is 1.23+0.22 kB in length. The mRNA encoding the C immunogen, exemplified by clones SP54 and SP59, is 1.12+0.08 kB in length. The mRNA encoding the H immunogen, exemplified by clone SO311, is 0.98+0.07 kB in length.

Native immunogens, B and C are isolated from E tenella by either gel filtration and identification with specific anti-CheY immunogen antibody or immunoaffinity chromatography using specific anti-CheY immunogen antibody. Eimeria tenella sporulated oocysts, about $1 \times 10^9$, are sonicated in a buffer, preferably phosphate buffered saline, containing about 0.1 mM PMSF for about 10 minutes, in about 2.5 minute bursts in an ice bath. The disrupted sporulated oocysts are collected by centrifugation at 27,000×g for 30 minutes at 4° C. The pellet is washed about 3 times with about 40 ml of PBS containing about 0.1 mM PMSF and recovered by centrifugation as described above. The washed pellet is resuspended in about 60 ml of about 5M guanidine-HCL/about 0.5M Tris-HCl, pH about 8.6, and about 400 mg dithiothreitol. Reduction was allowed to proceed for about 3 hours at 20° C. with mild agitation. Reduced and solubilized immunogen is obtained by centrifugation and collection of the supernatant fluid. The immunogen is concentrated to about 20 ml, preferably by ultrafiltration, and carboxymethylated by the addition of iodoacetic acid, about 400 mg. The pH is adjusted to about 8.6 by the addition of 3M Tris base and the reaction allowed to continue for about 60 minutes at about 20° C. in the dark. The guanidine-HCl is removed by dialysis against about 0.05M NH$_4$HCO$_3$, about 0.1 mg PMSF and about 0.02% sodium azide for about 48 hours. All insoluble material is removed by centrifugation. The supernatant fluid is concentrated by ultrafiltration and separated by gel filtration chromatography. The sample is applied to a column of Sephacryl S-200, about 87×2.5 cm, equilibrated in about 0.05M NH$_4$HCO$_3$, about 0.1% Zwittergent 3-12 and about 0.02% sodium azide. Fractions, about 4.5 ml, are collected at a flow rate of about 25 ml per hour and monitored at about 280 nm. The presence of *E. tenella* immunogen is determined by Western blotting, with rabbit anti-sporozoite antiserum and with antibody raised against the specific *E. tenella* recombinant fusion immunogens. The native immunogens are able to protect chickens against a coccidiosis infection.

Native *E. tenella* immunogens, A, B, C, H and F are isolated and purified form sporulated oocysts by immunoaffinity chromatography using antibody raised against the specific fusion immunogens. Affinity columns are prepared using preimmune serum and the specific fusion immunogen serum. Immunoglobulin G (IgG) fractions are prepared by the method of Corthier et al., J. Immunol. Meth. 66: 75-79 (1984) or by the carbonyldiimidazite method of Hearn et al., J. Biol. Chem. 254:2572-2574 (1979). About 15 mg of IgG is coupled to 0.5 gm of Sepharose-protein A (Sigma) using the method of Schneidert et al., J. Biol. Chem. 257:10766-10769 (1982). Approximately 5 mg of the reduced, carboxymethylated extract of *E. tenella* sporulated oocysts, prepared as described above, in about 0.1M borate buffer, pH 8.1, about 0.5M NaCl, about 0.02% sodium azide, and about 0.1 mM PMSF, is applied to the prebleed column equilibrated in the same buffer. The prebleed column was washed with 3 ml of column buffer and the combined column flow-through and washes are applied to the anti-*E. tenella* fusion immunogen column equilibrated in the same buffer. The column is washed with about 10 ml of column buffer and the native immunogen is eluted with about 3M sodium thiocyanate. The individual native immunogens are able to protect chickens against a coccidiosis infection.

Molecular weights and isoelectric points of Eimeria immunogens were also determined. Molecular weights were determined by analytical sodium dodecyl sulfate (SDS) polyacrylamide gel electrophoresis (PAGE) of samples prepared from sporulated oocysts and/or sporozoites of *E. tenella*, followed by transfer to nitrocellulose and immunodetection by Western Blotting as described above. Appropriate molecular weight controls are included. Isoelectric points were determined by Western Blotting of two dimensional gels run according to the procedure of O'Farrell, J. Biol. Chem. 250:4007-4021 (1975). Antibodies for both procedures are prepared as stated above. Immunogen A separated as a single band with a molecular weight of 24 kiloDaltons (kD). The predominant B immunogen is characterized as a diffuse doublet of 27-28 kD on SDS-PAGE with the minor immunogens appearing as faint bands suggesting some sharing of antigenic determinants within *E. tenella*. The minor bands have molecular weights of 22, 19, 18, 14, 12, 9, and 6 kD. The 27-28 doublet produces multiple spots on isoelectric focusing, in the range between pH 5.1 and 6 kD. The pIs of the faint additional bands detected by Western blotting were not determined. Immunogen C also migrates as a doublet with molecular weights of 21-22 kD. Immunogen H separates as two distinct major proteins with molecular weights of 28 and 18 kD and seven minor proteins with molecular weights of 27, 24, 23, 17, 14, 12, and 9 kDs. The Group F immunogen has a molecular weight of about 26-29 kD. The isoelectric points of immunogens A is 3.65 and H is 6.65. The isoelectric points of C and F have not been determined.

Poultry are administered an immunizing dosage of one or more of the recombinant derived *Eimeria tenella* immunogens described above. Immunogen administration to chickens may be by oral or parenteral routes or chicken embryos may be inoculated through the egg shell. Administration of immunogen by any of these routes may include an immunogen or immunogens given alone or as a solution or suspension with a physiologically acceptable medium. Such physiologically acceptable media include, but are not limited to, physiological saline, phosphate buffered saline, phosphate buffered saline glucose, buffered saline and the like. Parenteral administration includes inter alia, intramuscular, intraperitoneal, subcutaneous and intravenous injection or delivery of the *E. tenella* immunogens. Orally administered immunogens can be in the form of an aqueous solution or suspension. A suspension may include the immunogen in a gel composed of, for example, gelatins or alginates. Orally administered immunogens may also be included in the feed. Embryonated eggs are immunized by the injection of an immunogenic dose of one or more of the Eimeria immunogens. The immunogens for intramuscular and subcutaneous vaccination may be given along with an acceptable adjuvant. Acceptable adjuvants include, but are not limited to, Freund's complete, Freund's incomplete, double emulsions, anhydrous oils, alum-precipitate, water-in-oil emulsion containing Corynebacterium parvum and t-RNA The preferred adjuvant is alum-precipitate, in which the immunogen has been precipitated with aluminum hydroxide such as Alhydrogel ™. Immunization of chickens with recombinant derived *E. tenella* immunogens results in immunity to coccidiosis. Protective immunity is achieved by administration of from about 1.0 ng to about 100 $\mu$g, with about 100 ng to about 10 $\mu$g being preferred.

The following examples illustrate the present invention without, however, limiting the same thereto.

EXAMPLE 1

Preparation of Oocysts, Sporulated Oocysts, Sporozoites and Schizonts and the Corresponding Immunogens and Antigens

*Eimeria tenella* oocysts were isolated from cecal cores (coalesced masses of oocysts) from chickens infected 7 days earlier. *Eimeria acervulina* oocysts were isolated from feces and intestinal contents of chickens infected 5 to 6 days earlier. The isolated cecal cores and feces were separately disrupted in a Waring Blender (in distilled water), digested with pepsin (2 mg/ml) at pH 2.0 at 39° C. for 1 hour. Large amounts of debris and the pepsin were removed from pelleted material after centrifugation (1,000×g) in distilled water. A partially pure oocyst fraction was isolated from the pellet by flotation in 2.2M sucrose (Jackson, Parasitol, 54:87-93, 1964) and this crude material was further treated by incubating in cold Clorox (5.25% sodium hypochlorite, at 4° C.) for 10 minutes. The sodium hypochlorite was removed by several washes in sterile phosphate-buffered saline (PBS) pH 7.6 to obtain purified and sterile oocysts. Oocysts were sporulated in a shaking water bath at 20° C. for 48 hours (Edgar, Trans. Am. Micr. Soc. 62:

237–242, 1954). Sporulated oocysts were stored in PBS (pH 7.6) at 4° C.

Fully sporulated oocysts were sonicated on ice in a Bransonic cell disruptor, with a tapered probe. Sonication was performed using a 30 second on/off cycle to prevent overheating. Following this procedure, 90% breakage was achieved within 10–15 minutes. Detergent (Zwittergent 3–12, Calbiochem, 0 1% w/v) was added, and the mixture was stirred at 4° C. for 18 hours. After centrifugation at 27,000×g for 30 minutes, the supernatant was subjected to gel permeation chromatography on Sephadex S-200 (Pharmacia).

A column of Sephadex S-200 (8×44 cm) was equilibrated at 4° C. with 50 mg $Na_2HPO_4$-$NaH_2PO_4$, pH 7.2 and 0.1% Zwittergent 3–12. The sonicate was applied to the column, eluted with the same buffer and fractions collected (14 ml) and monitored by absorbance at 230 nm. Fractions were pooled according to the SDS-PAGE profile. Pooled fractions were dialysed against eight liters of 10 mM ammonium bicarbonate at 4° C. for one week with three changes of buffer, and were then freeze-dried. The lyophilized fractions were dissolved in glass-distilled water and were tested for in vivo activity, chicken protection. In vivo activity was routinely found between fractions 84–94. The protective Eimeria tenella fractions were pooled and designated Fraction V. For some batches, S-200 chromatography was performed in 50 mM ammonium bicarbonate, pH 7.7, containing 0.05% Zwittergent. This had no effect on the elution profile or on the in vivo efficacy.

Second generation schizonts were prepared from chicken intestinal cells four days post-infection according to the protocol of James, Parasitol, 80:301–312 (1980).

Immunogens for antibody production were prepared as follows. A 2 ml suspension of purified sporulated oocysts (5×10$^7$ per ml PBS, pH 7.6) was ground at 500 rpm for 5 minutes at 4° C. in a tissue homogenizer with a loose-fitting pestle (Patton, Science 150:767–760, 1965) and the supernatant fluid resulting from the disruption of the oocysts was removed after centrifugation (600×g for 10 minutes). The E. tenella pellet, composed of unbroken oocysts, sporocysts, and oocyst shells, was resuspended in an excysting solution containing 0.25% (w/v) trypsin (1:250) and 4.0% (w/v) taurodeoxycholic acid (Sigma) in Hanks balanced salt solution (pH 7.4) and incubated at 41° C. in 5% $CO_2$ (Patton et al, J. Parasitol. 65: 526–530, 1979). The E. acervulina pellet, also composed of unbroken oocysts, sporocysts and oocyst shells, was resuspended in an excysting solution containing 0.125% (w/v) trypsin (1:250) and 1.0% taurodeoxycholic acid in Hank's Balanced salt solution (pH 7.4) and incubated at 41° C. in an atmosphere containing 5% $CO_2$. Excystation was allowed to continue for ½ hour for E. acervulina and 1 hour for E. tenella after which the excysting solution was removed by centrifugation and parasite material was washed twice in phosphate buffered saline/glucose (PBSG) buffer of pH 8.0, ionic strength 0.145 containing 1% glucose, Schmatz et al., J. Protozool. 31:181–183, 1984. The parasite mixture was applied to a DE52 anion exchange column, equilibrated in PBSG, and purified sporozoites were eluted unretarded in the void volume (Schmatz et al., supra).

Sporozoites were freeze-thawed 3 times (dry ice to room temperature and sonicated until disrupted in PBS with 1 mM phenylmethylsulfonylfluoride as protease inhibitor to provide sporozoite antigen. Protein concentrations were determined by the method of Lowry et al., J. Biol. Chem. 193: 265–275, 1951 and antigens were stored in liquid $N_2$.

EXAMPLE 2

Production of Anti-*Eimeria tenella* Unsporulated, Oocyst, Sporulated Oocyst, Sporozoite, Schizont, Anti-Fraction V and Anti-*Eimeria acervulina* Sporozoite Antibodies Rabbits (New Zealand White, female) were multiply immunized with one of the various immunogens described in Example 1. Each immunization dose contained 50 μg of protein. The first immunization was given in Freunds complete adjuvant. Subsequent immunizations were given in Freunds incomplete adjuvant. The antigen adjuvant mixture was prepared by emulsifying 0.5 ml of antigen containing 50 μg protein in PBS with 0.5 ml of adjuvant. One ml of emulsion was then administered subcutaneously in multiple sites on a shaved area of the rabbit back. Secondary booster immunizations were given at approximately one month intervals following primary immunization. Animals were bled and immune sera prepared at approximately monthly intervals, starting six weeks after the start of the immunization schedule. Immune activity and specificity was determined by Western blot analysis using the specific extract antigens from Example 1 and the technique of Towbin et al., Proc. Natl. Acad. Sci. U.S.A. 76:4350–4354 (1979). Each antibody was specific for its corresponding immunogen, antigen.

EXAMPLE 3

Immunization of Two-Day-Old Chickens Against Coccidiosis with Fraction V Immunogens Broiler chicks were immunized with Fraction V immunogen as described in Example 1. The dosage was based on protein content as determined by the method of Lowry et al., J. Biol. Chem. 193:265–275 (1951) and was given intramuscularly on days 2, 9 and 16 following hatching. Experimental and control chickens were challenged one week after the last immunization with an oral inoculation of 5×10$^3$ E. tenella oocysts. Six days after challenge the chickens were killed and the severity of the lesions in the ceca were determined according to the method of Johnson and Reid, Exp. Parasitol. 28: 30–36 (1970).

The following results were obtained.

TABLE 4

| Immunogen | Dose (μg) | Number of Birds | Mean Group Lesion Score |
|---|---|---|---|
| Fraction V | 10.0 | 8 | 1.0 |
| Fraction V | 1.0 | 8 | 1.6 |
| Fraction V | 0.10 | 8 | 2.9 |
| None | — | 8 | 3.4 |

These results show that Fraction V immunogen can be used to immunize two day old chickens. An intramuscular inoculation provides a high level of protection against the disease as indicated by the absence of severe lesion development in immune birds after a normally virulent infection.

EXAMPLE 4

Preparation of Genomic DNA from *Eimeria tenella* Sporozoites

Purified *Eimeria tenella* sporozoites, from Example 1 were suspended in TE medium (10 mg Tris-HCl, pH 7.5, 0.1 mM EDTA) at a concentration of $1.5 \times 10^8$ sporozoites per ml. The dilute suspension of sporozoites was then adjusted to 0.5% in SDS (from a 20% SDS stock solution), and 15 mM in EDTA (from a 0.5 M-pH 8.0 stock solution) which resulted in both plasma and nuclear membrane lysis. The release of genomic DNA following nuclear lysis is marked by an obvious increase in the viscosity of the solution. To aid in solubilization, the solution was gently rocked at 50° C. on a platform for 30-60 minutes, and then digested for 3 hours at 50° C. with Proteinase K at a concentration of 100 μg per ml. Genomic DNA was purified by two extractions with phenol, two extractions with a mixture of phenol, chloroform and isoamyl alcohol (25:24:1), two extractions with chloroform and isoamyl alcohol (24:1), and two successive precipitations with sodium acetate/ethanol as described in Example 8. The nucleic acid pellet was washed twice with 70% ethanol and suspended in TE at an approximate concentration of $5 \times 10^8$ sporozoite equivalents per ml. The RNA component of the nucleic acid was selectively removed by digestion with heat inactivated RNase A at a concentration of 50 ug per ml for 60 minutes at 37° C. The RNase A and other residual proteins were removed by a secondary digestion with Proteinase K in 0.5% SDS and 15 mM EDTA for 3 hours at 50° C. as described above. Genomic DNA was then successively extracted with organic solvents, precipitated twice with ethanol, and then washed twice with 70% ethanol. The genomic DNA pellet was suspended in TE at a concentration of $2-3 \times 10^9$ sporozoite equivalents per ml and guantitated by absorbance at 260 nm. Undigested genomic DNA was then fractionated on an analytical gel to confirm (i) the spectrophotometric-derived concentration, (ii) the lack of residual RNA, and (iii) its high molecular weight integrity.

EXAMPLE 5

Construction of cDNA Expression Libraries

*E. tenella* oocysts, sporulated for seven hours, and sporozoites were prepared as previously described (Schmatz et al, supra; Wang & Stotish, J. Protozool. 22: 438-448, 1975). Total RNA was isolated from each stage either immediately after isolation (i.e. the sporozoites) or from cell pellets frozen in liquid nitrogen and stored at −80° C. (i.e., the 7 hour sporulating oocysts) by the method of Chirgwin et al., (Biochem. 18: 5294-5299, 1979). Due to the presence of the cell wall, oocyst samples were resuspended in 4 volumes of 4% guanidinium thiocyanate solution (volumes of solution relative to volume of cell pellet) and were sonicated for a total of 30 minutes at 20 W, 50% cycle with a Branson sonifier (Heat System Ultrasonics). Sporozoites were lysed upon the addition of the guanidinium thiocyanate stock solution (4M guanidinium thiocyanate, 0.5% N-lauroylsarcosine, 25 mM sodium citrate, pH 7.0, and 0.1M 2-mercaptoethanol); therefore sonication was unnecessary. The lysed cells were then centrifuged at 8,000 rpm for 10 minutes in a Beckmann JS-13 rotor at 10° C. to sediment particulate cellular debris. The supernatants were decanted into a clean flask and mixed with 0.025 volumes of 1M acetic acid and 0.75 volumes of absolute ethanol. The flask was shaken thoroughly and left to stand overnight at −20° C. to precipitate the nucleic acids. The next day, the RNA was collected by centrifugation in a Beckmann JS-13 rotor at 8000 rpm for 10 minutes at 10° C. The tubes were drained and the cell pellet was resuspended in 0.5 volumes of buffered guanidine hydrochloride stock solution (7.5M guanidine hydrochloride, 0.025M sodium citrate, pH 7.0, and 5 mM dithiothreitol). The volume of the guanidine hydrochloride stock solution is relative to the volume of the guanidinium thiocyanate solution previously used. The RNA was precipitated by adding 0.025 volumes of 1M acetic acid and 0.5 volumes of absolute ethanol. The solution was kept overnight at 20° C. and the RNA was collected once again by centrifugation. The guanidine hydrochloride precipitation was repeated, using half the volume of the guanidine hydrochloride stock solution used in the previous precipitation. The reprecipitated RNA was washed in 95% ethanol, dried, and resuspended in sterile water. This material was centrifuged for 30 minutes at 10,000 rpm (Beckmann JS-13 rotor) at 10° C. The supernatant fluids were saved and the pellets were resuspended in sterile water. The centrifugation step was repeated. The supernatant fluids were combined, mixed with 0.1 volume of 2M potassium acetate, pH 5, and 2 volumes of absolute ethanol, and were left to precipitate overnight at −20° C. The RNA pellets were collected by centrifugation at 10,000 rpm (Beckmann JS-13 rotor) for 30 minutes, dried, and resuspended in sterile water. The concentration of the RNA was determined by spectrophotometry.

Polyadenylated RNA was selected by oligo (dT)-cellulose chromatography (Aviv & Leder, Proc. Nat. Acad. Sci. U.S.A. 69: 1408-1412, 1972). To make a 1 ml column, 0.3 g of oligo (dT)-cellulose (Bethesda Research Laboratories, BRL) was resuspended in elution buffer (10 mM Tris-HCl, pH 7.5) and poured into a Pasteur pipette. Before use, the column was washed with 1% bed volumes of binding buffer (0.5M lithium chloride, 0.5% sodium dodecyl sulfate, 10 mM Tris-HCl, pH 7.5, and 1 mM ethylenediamine tetraacetic acid).

The RNA (0.5 mg), dissolved in sterile water, was heated at 68° C. for 5 minutes and cooled to room temperature on ice. An equal volume of 2X binding buffer was added, mixed thoroughly, and the sample was applied to the column. After washing the column with 50 mls of binding buffer, the poly(A+)-RNA was eluted with 10 mls of elution buffer. Ten, 1 ml fractions were collected and the concentration of RNA in each was determined by spectrophotometry at a wave length of 260 nM. The fractions with the highest absorbance were pooled and RNA was precipitated by adding 0.1 volumes of 2M potassium acetate, pH 5.0, and 2 volumes of absolute ethanol. The samples were left overnight at −20° C. and the RNA was collected by centrifugation as above. After precipitation, the samples were resuspended in sterile water and the concentration of each was redetermined by spectophotometry.

Starting with 7.5 μg of poly(A+)-RNA, first and second strand cDNA reactions were performed as described by Gubler and Hoffman (Gene 25:263-269, 1983). Synthesis of the first strand of the cDNA was carried out in a reaction volume of 40 ml containing 50 mM Tris-HCl, pH 8.3, 10 mM $MgCl_2$, 10 mM DTT, 4 mM Na-pyrophosphate. 1.25 mM dGTP, 1.25 mM dATP, 1.25 mM TTP, 0.5 mM dCTP, 15 μCi of [α-$^{32}$P] dCTP (3000 Ci/mmol), 100 μg/ml of oligo (dT$_{12-18}$), 3000 units AMV reverse transcriptase/ml (Beard, Life Sciences, St. Petersburg, Fla.) for 30 minutes at 42° C. The products were extracted with phenol/chloroform and precipitated with absolute ethanol out of 2M NH$_4$-acetate, Okayama & Berg, Mol. Cell Biol. 2: 161-170, 1982. The pellets were washed with 70% ethanol, dried, and resuspended in 40 μl of sterile water.

For second strand synthesis, 500 ng of single-stranded cDNA (i.e. 1 μg of the cDNA/mRNA hybrid) was resuspended in 100 μl of 20 mM TRIS-HCl, pH 7.5, 5 mM MgCl$_2$, 10 mM (NH$_4$)$_2$SO$_4$, 100 mM KCl, 0.15 mM β-AND, 50 μg per ml BSA, 40 μM each of dATP, dGTP, dCTP and dTTP, 8.5 units/ml of E. coli RNase H (Pharmacia P-L Biochemicals, Inc.) and 230 units per ml E. coli DNA polymerase I (Pharmacia P-L Biochemicals, Inc.). Incubations were sequentially carried out at 12° C. for 60 minutes and at 22° C. for 60 minutes. EDTA was added to 20 mM to stop the reaction and the products were extracted twice with phenol/chloroform. The double stranded cDNA was precipitated with 2 volumes of absolute ethanol from 2M NH$_4$-acetate as previously described.

The cDNA (500 ng-1 μg) was then methylated in a 20 μl volume of IX EcoRI methylase buffer containing 50 mM Tris-HCl, pH 7.5, 1 mM EDTA, 5 mM DTT, and 10 μM S-adenosylmethionine. The reaction was carried out at 20° C. for 20 minutes after the addition of 20 U of EcoRI methylase (New England Biolabs). To terminate the reaction, the enzyme was heat inactivated for 15 minutes at 70° C. The samples were cooled on ice and the cDNA was blunt-ended as follows. To the tube containing 21 μl of EcoRI-methylated cDNA, 2.5 μl of 0.1M MgCl$_2$, 2.5 μl of 0.2 mM d (A, C, G, T) TP and 5 units of T4 DNA polymerase (BRL) were added. The reaction was carried out at 20°-22° C. for 10 minutes and terminated with the addition of EDTA to a final concentration of 15 mM. The reaction products were extracted twice with phenol/chloroform and precipitated with ethanol as above.

The pellets from the previous reactions were resuspended in 4.5 μl of 100 μg/ml kinased EcoRI dexanucleotide linkers (BRL) in buffer containing 70 mM Tris-HCl, pH 7.6, 10 mM MgCl$_2$, 5 mM DTT, and 1 mM ATP. T4 DNA ligase (New England Biolabs, 200 U/0.5 μl) was added and the reaction mixture was incubated overnight at 12° C. The linker ligated cDNA's were then digested to completion with EcoRI (BRL). To the 5.5 μl overnight incubation, 5 μl of EcoRI correcting buffer (50 mM Tris-HCl, pH 7.5, 10 mM MgSO$_4$, 200 mM NaCl) was added. The mixture was heated for 10 minutes at 70° C. to inactivate the ligase. The volume of the reaction mixture was increased two-fold (to 20 μl) with 100 mM Tris-HCl, pH 7.5, 50 mM NaCl, and 10 mM MgCl$_2$ and 2 μl of EcoRI restriction endonuclease (16 units/ul) was added. The digest was allowed to proceed for one hour at 37° C. after which the enzyme was heat inactivated for 20 minutes at 65° C. The products were precipitated as above.

To remove the digested linkers from the reaction mixture, the cDNA was further purified on an Elutip-d column (Schleicher and Schuell). Finally. the cDNA (300 ng) was ligated into 7.5 μg of commercially purchased EcoRI-digested, alkaline phosphatase treated λgt11 vector DNA (Promega Biotec). The vector-to-donor molar ratio in the ligation mixture was 1:1, and the final concentration of DNA was approximately 200 μg/ml. The ligation reaction was carried out in 10 mM Tris-HCl, pH 7.5, 10 mM MgCl$_2$. To anneal the cohesive ends of the λ vector, the mixture was first incubated at 42° C. for 15 minutes. It was then supplemented with 1 mM ATP, 10 mM DTT, and 40,000 units/ml of T4 DNA ligase (New England Biolabs). The reaction was incubated overnight at 14° C.

The λ vector hybrids were packaged in vitro with commercially available packaging extracts according to the manufacturer's instruction (Amersham). Small aliquots of the packaged phage were transduced into Escherichia coli host strain Y1088 (Huynh et al., In "DNA cloning: A practical approach", Volume I, Glover, D. ed., IRL Press, Oxford, pp 49-78, 1985) and these were plated on LB plates using 2.5 ml of LB (10 g per L Bactotryptone, 5 g per L Bacto-yeast extract, 10 g per L NaCl, pH 7.5) soft agar containing 600 μg ml$^{-1}$ X-gal and 16 mM IPTG. Two cDNA libraries, each consisting of approximately 1×10$^7$ independent recombinant phage clones were generated. The nonrecombinant background, as determined by growth on X-gal/IPTG plates, was estimated to be 13%.

EXAMPLE 6

Screening of λgt11 cDNA Libraries

The screening of the cDNA libraries from Example 5 with either anti-Fraction V antibody or anti-sporozoite antibody, from Example 2, was done essentially as described by Huynh et al., supra. Packaged phage from the unamplifigd cDNA library were transduced into E. coli strain Y1090 and plated on 150 mm plates at a density of 0.5-1.0×10$^5$ plaque forming units (pfu) per plate. The plates were incubated at 42° C. for 3.5 hours, overlaid with dry nitrocellulose filters presoaked in 10 mM IPTG, and incubated overnight at 37° C. The filters were removed, blocked for 1 hour with 20% fetal calf serum in Tris buffered saline (TBS; 50 mM Tris HCl/150 mM NaCl, pH 8.0) containing 0.05% Tween 2% (TBST), and were then incubated with the appropriate antibody for an equivalent length of time. Antibody binding sites were detected with [$^{125}$I] labeled protein A. Positive plaques were picked, replated, and rescreened until each clone was shown to be plaque pure.

For cross-screening experiments, 1 μl of phage lysate from each plague purified clone was spotted on a lawn of E. coli Y1090 cells. Recombinant fusion proteins were induced, transferred to nitrocellulose, and immunoblotted as described below. Screening and cross-screening with the various antisera revealed the five groups of clones in Table 1. All of the antisera used for immunoblotting were exhaustively preabsorbed with a concentrated lysate of λgt11 lysogen BNN93. After preabsorption, they were diluted 1:100 in TBST and stored at 4° C. until required.

Monospecific antibodies to each of the recombinant phage were affinity purified from polyspecific antisera, from Example 2, by a modification of the method of Hall et al. (Nature 311: 379-382, 1984) and by immunizing rabbits as described in Example 2 with the purified recombinant E. tenella-CheY fusion proteins as described in Example 13. The fusion proteins included Group A, SO67-CheY; Group B, SO7-CheY, Group C, SP54-CheY; Group H, SO311-CheY; and Group F, SO216-CheY. Filter plaque lifts were prepared from purified recombinant clones as was done for screening. Approximately 2×10$^5$ pfu were plated per 150 mm plate to give close to semiconfluent lysis at the end of the 37° incubation period. The nitrocellulose was then removed, blocked with 20% fetal calf serum in TBST for 4 hours, and incubated overnight with 20 ml of preabsorbed polyspecific serum (diluted 1:20 with 20% fetal calf serum in TBST containing 0.02% NaN$_3$). All of the incubations were done at room temperature with constant agitation. Subsequently, the filters were washed five times for 20 minutes each with 50 ml of TBST and one time with 0.15 % NaCl/0.05% Tween 20. The antibodies were eluted from each of the filters with 10 ml of 0.2M glycine-HCl/0.15M, NaCl/0.05% Tween 20, pH 2.8 for 30 minutes. The pH of each eluate was restored to 8.0 with Tris base and the recombinant eluted antibodies (REA's) were stored at −20° C. until required.

Parasite antigens were obtained by sonicating unsporulated oocysts, sporulated oocysts, and DE-52 purified sporozoites in NET buffer (50 mM Tris-HCl, pH 7.5, 150 mM NaCl, 5 mM EDTA) with 1 mM phenylmethylsulfonylfluoride (PMSF) as a protease inhibitor as described in Example 1. Protein concentrations of each sample were determined by method of Lowry et al., supra. The yield of antigen from $3 \times 10^5$ unsporulated/sporulated oocysts was approximately 50 μg, whereas the same amount of antigen was obtained from approximately $2 \times 10^6$ sporozoites. Samples were kept at 20° C. until ready for use. For blots of parasite antigens, 50 μg of each sonicated sample was mixed with an equal volume of 2x sample buffer (0.125 Tris-HCl, pH 6.8, 4% w/v SDS, 10% v/v 2-mercaptoethanol, 20% glycerol and 0.0025% bromophenol blue), boiled for 3 minutes and electrophoresed on either a 15% SDS-polyacrylamide gel or a 5–20% SDS-polyacrylamide gradient gel (Laemmli, Nature 227:680–684, 1970).

Alternatively antigens were prepared by resuspending oocysts at a concentration of $5 \times 10^7$ per ml and sporozoites at a concentration of $5 \times 10^8$ per ml in NET buffer containing a cocktail of protease inhibitors (2 mg ml$^{-1}$ 1–10 phenanthroline, 2 mM ml$^{-1}$ benzamidine, 0.002 mg ml$^{-1}$ PMSF, 0.048 mg ml$^{-1}$ Sigma soybean trypsin inhibitor, 0.048 mM ml$^{-1}$ aprotinin, 0.02 mg ml$^{-1}$ leupeptin). At this point the samples were mixed with an equal volume of 2x sample buffer without bromophenol blue. The samples were boiled for 3 minutes, sonicated till fully disrupted, and reboiled again for 3 minutes. Bromophenol blue was added to 0.0025% and the samples were stored at −20° C. until ready for use. For immunoblotting, oocyst or sporozoite antigens were loaded and subjected to electrophoresis as stated above.

Proteins separated by SDS-PAGE were electrophoretically transferred to nitrocellulose by the technique of Towbin et al., Proc. Natl. Acad. Sci. U.S.A., 76:4350–4354 (1979). The nitrocellulose was subsequently blocked with 20% fetal calf serum in TBST for 4 hours. After blocking, the nitrocellulose was incubated overnight at room temperature in 20 ml of antibody diluted with 20% fetal calf serum in TBST containing 0.02% NaN$_3$. Polyspecific antisera were diluted 1:100 to 1:200 and monospecific recombinant eluted antisera were diluted 1:10. Following the contacting with specific antibody, the filters were washed three times for 5 minutes each with 200 ml of TBST. Bound antibody was detected with $^{125}$I-protein A diluted in 20 ml of TBST to a final concentration of $2 \times 10^5$ counts per minute ml$^{-1}$. Incubation with radiolabelled protein A was carried out for 1 hour at room temperature after which time the filters were again washed three times for 5 minutes with 200 ml of TBST, were air dried, and exposed to Kodak X-omat AR film.

Alternatively, the nitrocellulose was blocked with 0.5% gelatin in phosphate buffered saline, pH 7.4, for 1 hour with three 200 ml washes followed by a second blocking with 0.25% gelatin in TEN buffer, 50 mM Tris-HCl, 150 mM NaCl, 5 mM EDTA, pH 7.4, for 1 hour and washed as before. After blocking, the nitrocellulose was incubated overnight at room temperature in 20 ml of antibody diluted 1:100 to 1:200 with TEN buffer containing 0.25% gelatin and 0.05% Triton X-100. The filters were washed 5 times for 20 minutes each with 200 ml of TEN containing 0.25% gelatin. Bound antibody was detected with $^{125}$I-protein A diluted in 20 ml of TEN, 0.25% gelatin, 0.05% Triton to a final concentration of $2 \times 10^5$ cpm ml$^{-1}$. Incubation with radiolabelled protein A was carried out for 1 hour at room temperature, after which time the filters were washed 2 times for 15 minutes with 200 ml of TEN containing .25% gelatin and 0.05% Triton and 4 times for 15 minutes with 200 ml of TEN. After washing, the filters were air dried and exposed to Kodak X-omat AR film.

EXAMPLE 7

Preparation of phage DNA

Recombinant and wild type λgtll phage from Example 6, were introduced as lysogens into *E. coli* host strain Y1089 (Huynh et al., supra) at a multiplicity of 10. The lysogens were streaked on to LB-plates containing 100 μg ml$^{-1}$ ampicillin for single colony isolation and incubated overnight at 30°–32° C. The growth of several colonies was checked at 32° C. and 42° C. One colony was picked from a 32° C. plate that did not grow at 42° C., and an overnight culture was set up in LB broth with 50 mg L$^{-1}$ ampicillin.

The lysogenized clones were then grown from the overnight culture in 50 ml of LB broth containing 50 μg ml$^{-1}$ ampicillin at 32° C. until an O.D. 600 of 0.3 to 0.5 was reached. Phage excision and replication was induced by a temperature shift to 45° C. for 20 minutes. Continued phage replication was insured by continuing to grow the cultures at 37° C. for 2 to 3 hours, until sign of cell lysis was visible. If the cultures were not completely lysed, 0.1 ml of chloroform was added to each, and the cultures were agitated for an additional 10 minutes at 37° C. Under these conditions, lysis of the cells occurs after a few minutes. The cellular debris was routinely removed, at this point, by centrifugation for 5 minutes at 7,000 rpm in a Beckmann JS-13 rotor. The phage supernatant fluids were stored overnight at 4° C. after adding MgSO$_4$ to a final concentration of 0.01M, to stabilize the phage heads.

After bringing the phage supernatant fluids to room temperature, 50 μl of 10 mg ml$^{-1}$ DNase I and 25 μl of 10 mM ml$^{-1}$ RNase A were added to each sample. These were incubated for minimally one hour at 30° C., after which 1.46 gm of NaCl was added and thoroughly dissolved in each. The supernatant fluids were incubated further on ice for a minimal time of 30 minutes. The remaining cellular debris was then collected by centrifugation for 10 minutes at 10,000 rpm in a Beckmann JS-13 rotor. The supernatants were collected from each sample and in each supernatant fluid, 3.5 gm of Carbowax pEG 8000 (polyethyleneglycol 2000, Fisher Scientific Co.) was dissolved. In the presence of PEG, the phage heads were left to precipitate overnight at 4° C. The next day, the phage heads were collected by centrifugation. The supernatant fluids were centrifuged for 10 minutes at 10,000 rpm in a Beckmann JS-13 rotor maintained at 4° C. The supernatant fluids were carefully drained off and discarded. The pellets were resuspended in 250 μl of 0.1M Tris-HCl (pH 7.9), 0.3M NaCl, and 1 mM EDTA, after which 12.5 μl of 0.5M EDTA was added to chelate any free Mg++ left behind in the sample. The phage heads were incubated in the aforementioned buffer for 10 minutes at 67° C. After the incubation, 5 μl of 10% SDS was added to each sample and the samples were mixed on a vortex mixer. Heating was used to denature the phage proteins. The SDS completes the denaturation step, and releases the DNA from the phage heads.

The DNA which has been released from the phage is then extracted twice with phenol, three times with chloroform-isoamyl alcohol (24:1), and precipitated with the addition of one-tenth volume of 3M NaOAc (pH 7.5) and two volumes of absolute ethanol. The samples were left to precipitate overnight at −20° C. The next day, the DNA was collected by centrifugation in a microfuge for 20 minutes. The precipitated DNA was redissolved in 300 μl of 0.3M KOAc and reprecipitated with the addition of two volumes of absolute ethanol. The samples were incubated at −80° C. for 10 minutes and the DNA was collected by centrifugation as described above. The DNA pellets were washed with 70% ethanol, dried, and r(R)suspended in 100 μl of TE buffer (10 mM Tris-HCl (pH 7.6), 1 mM EDTA (pH 8.0) The concentration of DNA in each sample was determined by spectrophotometry at a wavelength of 260 nM.

EXAMPLE 8

Purification of cDNA Insert From λgtll Clones

Ten to 20 μg of λgtll recombinant phage, from Example 7, (at a final DNA concentration of 0.2 μg/μl) was cut to completion with EcoRI (80U/μl; Boehringer Mannheim) in a reaction buffer composed of 50 mM NaCl/100 mM Tris-HCl (pH 7.5)/5 mM MgCl₂. The reaction was conducted at 37° C. for 4 hours using a 5-fold enzyme excess. Reaction products were adjusted to 0.3M sodium acetate by the addition of one-tenth volume of a 3M (pH 5.6) stock solution, precipitated with 2.5 volumes of ethanol, chilled for 20 minutes at −70° C., and collected by centrifugation at 15,000×g for 15 minutes at 4° C. The pellet was suspended in 30 μl of TE (10 mM Tris-HCl, pH 7.5/0.1 mM EDTA) and loaded onto a preparative 1% agarose flat bed gel containing ethidium bromide. The insert was resolved from the phage arms by electrophoresis overnight (15 hr/60 mA).

Fractionation of the insert was verified by visualization under ultraviolet light. The agarose gel was sliced on both sides of the cDNA insert and pieces of NA-45 membrane (Schleicher & Schuell) were inserted into the gel, "sandwiching" the cDNA insert. The insert was then electrophoresed onto the NA-45 membrane. Upon completion, the membrane was removed from the gel, cut into small pieces and placed into an Eppendorf tube with 250 μl of a solution composed of 50 mM arginine (free base). 1M NaCl. DNA was eluted from the membrane at 70° C. for 3 hr; the aqueous solution was removed and the elution process was repeated using a fresh 250 μl of eluant. The two eluates (totaling 500 μl) were combined and chilled to 4° C. Insoluble particulates were collected by centrifugation for 10 minutes at 4° C. at 15,000×g. The soluble material was then extracted twice with phenol, twice with phenol/chloroform/isoamyl alcohol (25:24:1) and twice with chloroform/isoamyl alcohol (24:1). DNA was precipitated with 0.3M sodium acetate/EtOH (as described above), washed twice with 70% EtOH, air dried, suspended in 25 μl of TE and guantitated by absorbance at 260 nM. An aliquot of the DNA was then analyzed on an analytical agarose gel for confirmation.

EXAMPLE 9

Mapping of cDNA clones isolated from λgtll library

DNA inserts, from Example 8, were isolated from phage clones representative of Group A (SO6', SP1, SO67), Group B (SO9, SO24, SO7', SO1'), Group C (SP54, SP59) Group H (SO311, SO227, SO231) and Group F (SO216). The phage inserts were subcloned into the plasmid vector, pucl8, which is commercially available from Bethesda Research Lab. Both the isolation of inserts as well as the subcloning were done as described for the CheY vector, pJC264 in Example 12. The plasmids were grown as mini-preparations in 5 ml cultures of LB broth, and the DNA was isolated from each, using the alkaline lysis method as described in Example 12. The DNA was resuspended in 50 μl of TE buffer, 10 mM Tris-HCl (pH 8.0), 1 mM EDTA (pH 8.0), containing DNase-free pancreatic RNase (200 g ml⁻¹) and by brief vortex mixing. The DNA samples were then digested with a variety of restriction endonucleases (commercially available from many suppliers including Bethesda Research Laboratories) in order to determine which were cutters or noncutters of the cDNA inserts. The restriction enzyme digestions were always done according to the manufacturer's recommendations. Usually five cutters were chosen for each clone, and a mapping analysis was conducted by doing single and double digests of each recombinant plasmid. The DNA fragments which were generated were separated electrophoretically on 1% agarose gels, and sized by comparison to DNA markers which were run simultaneously on the same gels. Maps were constructed of each clone by entering the fragment size data and known vector restriction sites into the Intelligenetics Restriction Map Generator program (MAP Intelligenetics, Inc.). In each case, the map which is the most compatible with all of the data is shown in the Figures I-V.

EXAMPLE 10

Construction Of The CheY-ANF Plasmid

An expression plasmid for the fusion polypeptide SCIN-(rat-ANF-26) was derived from the pSCNI plasmid. The pSCNI plasmid is a bacterial-expression plasmid for the N-terminal 165 amino acids of the yeast RASI protein SCIN and is described in Temeles et al., Nature 313: 700–703 (1985). The plasmid pSCIN (1 μg) was digested to completion with AccI, and the ends were filled in with *E. coli* DNA polymerase I large fragment (Klenow polymerase). The synthetic ANF gene was excised by digestion of pANF-1 with DdeI and Hinc II. After filling out the DdeI end with Klenow polymerase, the 104 bp fragment was isolated. The ANF gene fragment was then ligated to pSCIN treated as described above and used to transform competent JM105 cells. Ampicillin-resistant colonies were screened with an appropriate oligonucleotide. SDS extracts of hybridization positive colonies were electrophoresed on a 15% sodium dodecyl sulfate polyacrylamide gel (SDS-PAGE), followed by either staining with Coomassie Blue or protein blot analysis to detect the expression of the fusion protein.

Figure 6:
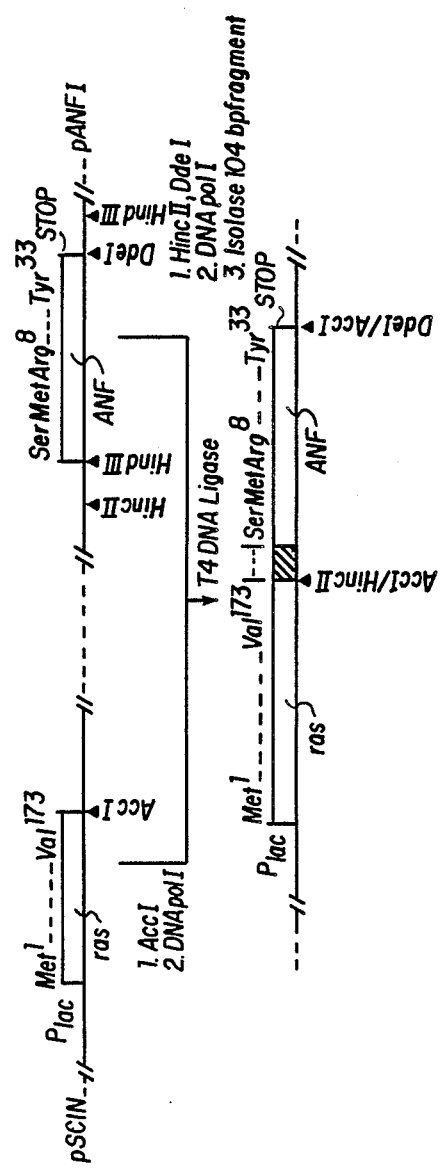
FIG. 6 is a diagram of the pSC1N plasmid.

The ANF gene was transfered from the pSCNI plasmid to the pLCl-28 plasmid. Plasmid pLCl-28 is a col El-derived plasmid that contains the entire Che operon and is described in Matsumura et al., J. Bacteriol. 160: 36–41 (1985). The Che operon fragment containing the 3' portion of the Che B gene and the CheY and CHeZ genes was excised from pLCl-28 as a BamHI HindIII fragment and sub cloned into BamHI-Hind III digested pUCl3(PL Biochemicals) to give pUCl3-CheY-CheZ. *Escherichia coli* JM105 clones transformed by pUCl3-CheY-CheZ expressed CheY and CheZ polypeptides off the lac promoter contributed by the pUCl3 vector. To construct an expression plasmid for the CheY-(rat-ANF-26) fusion, pUCl3-CheY-CheZ was digested at the unique PstI site internal to the CheY coding region and at the unique SmaI site in the pUCl3 polylinker 3 to the inserted Che DNA. The resulting 3 kb PstI-SmaI fragment containing the pUCl3 vector and the DNA encoding the N-terminal 100 residues of CheY was recombined with the 160 bp Pst 1-HindIII fragment of pSCNl-(rat-ANF-26) that encodes the Met-(rat-ANF-26) sequence and contains 50 bp of untranslated RASI sequence 3' to the termination codon for the ANF peptide, see FIG. 6. *E. coli* JM105 was transformed with the ligation mix containing the two fragments described above. DNA was isolated (minipreps) from ampicillin-resistant clones. The desired clones were identified as those releasing a 160 bp gene fragment upon EcoRI-Pst I digestion. These clones were shown to express ANF eptides by Western Blot analysis of total cellular protein using anti-ANF antisera.

EXAMPLE 11

Construction of Plasmid pJC264

The CheY-ANF plasmid from Example 10 was converted to the plasmid pJC220 which was in turn modified to produce the unique pJC264 plasmid. To convert CheY-ANF to PJC220, 40 μg of CheY-ANF plasmid DNA was incubated at 37° C. with 20 units of HindIII (International Biotechnologies, Incorporated) in a final volume of 200 μl of 25 mM Tris-HCl pH 7.8, 50 mM NaCl, 10 mM MgCl$_2$, 1 mM dithiothreitol, and 100 μg/ml bovine serum albumin. At 15 minute intervals 50 μl aliquots were transferred to tubes containing 2 μl 0.5M Na-EDTA, pH 8.0 to stop the digestion. Each sample 150 ng was electrophoresed in adjacent lanes of a 0.7% (w/v) Seaplaque agarose (FMC) gel containing 89 mM TRIS, 89 mM boric acid, 2 mM EDTA (TBE) and 0.5 μg/ml ethidium bromide. The linearized plasmid was identified as that band comigrating with XhoI-digested CheY-ANF when visualized by 365 nm light. This band was excised from the gel with a razor blade from the lanes corresponding to 15, 30, 45 and 60 minutes of digestion, melted at 65° C., and diluted with 10 volumes of 0.2M NaCl, 10 mM Tris-HCl pH 7.2, 1 mM EDTA, at 37° C. (Buffer A). The DNA was bound to a NACS Prepac cartridge (Bethesda Research Laboratories) BRL by gravity flow, washed with 10 ml Buffer A, and eluted with 0.5 ml Buffer D (2M NaCl, 10 mM Tris-HCl pH 7.2, 1 mM EDTA) by gravity flow. One ml absolute ethanol was added to the column eluate. The sample was mixed and incubated on dry ice 10 minutes and centrifuged at 12,000×g for 15 minutes at 4° C. The supernatant fluid was decanted, the precipitate was washed with 0.5 ml 70% ethanol and dried in vacuo. After dissolving the pellet in TE (10 mM Tris-HCl pH 7.4, 1 mM EDTA), the DNA content was measured by the ethidium bromide spot test, agarose plate method (Maniatis et al., Molecular Cloning: A Laboratory Manual, Cold Spring Harbor Laboratory (1982) p. 468–469).

The ends of the linearized plasmid DNA were made blunt by incubating 30 ng for 2 hours at 15° C. in a 25 μl reaction mix containing 20 μM each of dATP, dGTP, dCTP, and TTP, 60 mM NaCl, 6 mM Tris-HCl pH 7.5, 6 mM MgCl$_2$, 1 mM dithiothreitol, and 22.5 units of DNA Polymerase I, large (Klenow) fragment (Boehringer-Mannheim). The reaction was terminated and the DNA purified by extraction with phenol/chloroform (Maniatis et al., supra, p. 458–459) and ethanol precipitation (Maniatis et al., supra, p. 461).

BamHI linkers (d GGGATCCC, Boehringer-Mannheim), 12.5 μg, were phosphorylated with 40 units of T4 polynucleotide kinase (Pharmacia) in a 40 μl reaction mixture containing 50 mM Tris-HCl pH 7.4, 10 mM MgCl$_2$, 5 mM dithiothreitol, 500 μM ATP, and 40 μCi of $\gamma$-$^{32}$P-ATP (Amersham, 5000 Ci/mmol, 10 mCi/ml), for 30 minutes at 37° C. The reaction was stopped by incubating at 70° C. for 5 minutes, and the linkers were stored at −20° C. until used.

The blunt-ended, linearized plasmid DNA was dissolved in 6.6 μl water and adjusted to a 10 μl final volume containing 125 ng phosphorylated BamHI linkers, 6.6 mM Tris-HCl pH 7.5, 6.6 mM MgCl$_2$, 1 mM ATP, 10 mM dithiothreitol, and 0.0025 units T4 DNA ligase (New England Biolabs). After incubating 18 hours at 4° C., 5 μl of this mixture were added to 100 μl competent *E. coli* HB101 cells (BRL). Transformation of cells was performed according to the method provided by BRL. Eleven ampicillin-resistant colonies were chosen at random and each was used to inoculate 5 ml liquid culture of LB broth (Maniatis et al., supra) containing 100 μg/ml ampicillin. After overnight growth at 37° C., plasmid minipreps were made as described by Ish-Horowicz and Burke, Nucleic Acids Research 9:2989–2998 (1981).

By restriction enzyme mapping and agarose gel analysis, one plasmid, designated pJC220, was found to have at least one BamHI linker in place of the promoter-proximal HindIII site. This plasmid was also shown to retain the HindIII site (now unique) at the 3' end of the CheY coding region.

The pJC220 plasmid was converted to the pJC264 plasmid by digestion of 10 μg of pJC220 DNA with 50 units of HindIII (Boehringer-Mannheim) for 1 hour at 37° C. in a 50 μl solution containing 50 mM NaCl, 10 mM Tris-HCl pH 7.4, 10 mM MgSO$_4$, and 1 mM dithiothreitol. Ammonium acetate was added to 2.5M final concentration, and the DNA recovered by precipitation with 2 volumes of ethanol. The HindIII digested DNA was then partially filled in with 5 units of the large fragment of DNA polymerase I (Boehringer-Mannheim) in a 20 μl solution containing 20 μM each dATP and dGTP, 60 mM NaCl, 6 mM Tris-HCl, pH 7.5, 6 mM MgCl$_2$, and 1 mM dithiothreitol, and incubated 30 minutes at room temperature. The sample was extracted with phenol/chloroform and recovered by ethanol precipitation as described by Maniatis et al, Molecular Cloning. A Laboratory Manual. Cold Spring Harbor Laboratory (1982).

The DNA was dissolved in water and adjusted to 0.3M NaCl, 30 mM Na acetate pH 4.6, and 4.5 mM $ZnCl_2$, in a final volume of 20 $\mu$l. Five units of S1 nuclease (BRL) were added and the mixture incubated at 37° C. for 30 minutes. Digestion was stopped by adding 1 $\mu$l 0.5M EDTA pH 8.0, and the DNA was phenol/chloroform extracted and ethanol precipitated. The S1-nuclease treated DNA was digested with 80 units of EcoRI (New England Biolabs) in 50 $\mu$l of buffer containing 100 mM NaCl, 50 mM Tris-HCl pH 7.4, and 10 mM $MgSO_4$, for 30 minutes at 37° C. DNA was recovered by ethanol precipitation in ammonium acetate as described above. The EcoRI ends were filled in with the large fragment of DNA polymerase I as described above, but in the presence of dATP and TTP and in the absence of dGTP and dCTP. DNA was extracted with phenol/chloroform and recovered by ethanol precipitation.

One hundred ng of this DNA were ligated for 24 hours at 4° C. in 10 $\mu$l of solution containing 66 mM Tris-HCl pH 7.5, 6.6 mM $MgCl_2$, 10 mM dithiothreitol, 1 mM ATP, and 400 units T4 DNA ligase (New England Biolabs). Two $\mu$l of ligation mix were used to transform 100 $\mu$l of competent *E. coli* JM109 cells (Stratagene) using the supplier's standard procedure. Ampicillin-resistant transformants were screened by colony hybridization using a 5'-$^{32}$P labeled synthetic oligonucleotide d(CCCAAGAATTCACTGG) as a probe, using standard methods of Mason & Williams, in "Nucleic Acid Hybridization: A Practical Approach", B. D. Hames and S. J. Higgens, eds. IRL Press (1985), p. 113-137. One hybridizing colony, designated pJC264, was shown by restriction mapping to have reconstructed a unique EcoRI site at the 3' end of the CheY gene.

The construction of pJC264 from CheY-ANF can be seen schematically in FIG. 7 and the restriction map of pJC264 is shown in FIG. 8.

EXAMPLE 12

Subcloning cDNA Inserts Into pJC264

Twenty micrograms of pJC264 from Example 11 was linearized with EcoRI using the reaction conditions described in Example 8. The reaction product was precipitated, washed twice with 70% EtOH and suspended in 43 $\mu$l of distilled water and 5 $\mu$l of 10X CIP buffer (0.5 M Tris-HCl, pH 9.0, 10 mM $MgCl_2$, 1 mM $ZnCl_2$, 10 mM spermidine). The 5' phosphate from the EcoRI ends was removed with calf intestinal alkaline phosphatase (Boehringer-Mannheim). One microliter of enzyme (19 U/ul) was added to initiate the reaction at 37° C. for 30 minutes and then a second microliter was added for an equivalent length of time. The reaction was stopped by the addition of 42.5 $\mu$l distilled water, 2.5 $\mu$l 20% sodium dodecyl sulfate (SDS), 10 $\mu$l 10X STE (100 mM Tris-HCl, pH 8.0/1M NaCl/10 mM EDTA) and heated at 68° C. for 15 minutes. The reaction mixture was then extracted twice with phenol/chloroform/isoamyl alcohol (48:48:2), twice with chloroform/isoamyl alcohol (24:1), and the final aqueous phase was passed through a 1 cc column bed of Sephadex G-25 (medium) equilibrated in TE by centrifugation at 1000$\times$g for 5 minutes at room temperature (spin-column). The DNA was then precipitated as described earlier, washed twice with 70% EtOH, suspended in 50 $\mu$l of TE and quantitated by absorbance at 260 nm.

Approximately 100 ng of EcoRI linearized and phosphatased pJC264 was mixed with an equimolar amount of gel purified *Eimeria tenella* cDNA insert in a 20 $\mu$l reaction mixture which, in addition, consisted of 66 mM Tris-HCl, pH 7.6, 5 mM $MgCl_2$, 5 mM dithiothreitol, 1 mM ATP. The reaction was initiated by the addition of 1 $\mu$l of T4 DNA ligase (New England Biolabs, 200-400 U/ul) and proceeded at 14° C. for 12-16 hours.

A predetermined volume (3 ml per transformation reaction) of 2$\times$YT bacterial media (16 g bactotryptone/10 g yeast extract/5 g NaCl per liter) was inoculated with a single colony of *E. coli* JM83 and grown with vigorous mixing at 37° C. until it reached an optical density at 600 nm of 0.6. Bacteria were collected by centrifugation at 1000$\times$g at 4° C. for 5 minutes and gently suspended in one-half of the original culture volume with sterile 50 mM $CaCl_2$. The suspension was kept on ice for 20 minutes and the bacterial cells were collected by centrifugation as above. The pellet was then gently suspended in one-tenth volume of sterile 50mM $CaCl_2$. The bacterial suspension was then kept at 4° C. for 16-24 hours.

The 20 $\mu$l ligation reaction mixture was diluted to 100 $\mu$l by the addition of 80 $\mu$l of sterile TE, and 5 $\mu$l and 95 $\mu$l aliquots were dispensed to sterile polypropylene tubes. Approximately 200 $\mu$l of competent bacteria were added to each of the tubes containing the ligation reactions (as well as the appropriate ligation and transformation controls) and these were placed on ice for 40 minutes. After this, the bacteria were "heat shocked" by incubation at 42° C. for 90 seconds. Each transformation tube was then plated onto a 2$\times$YT agar plate which contained ampicillin at a concentration of 50 mg/l for the selection of bacteria harboring plasmids and for plasmid maintenance. Plates were incubated in an inverted position overnight at 37° C.

Bacterial clones harboring plasmids were identified by their ability to grow on plates in the presence of drug selection. Single colonies were used to inoculate 5 ml of 2$\times$YT/AMP (i.e., 2$\times$YT media containing ampicillin at 50 mg/L) and these cultures were grown overnight at 37° C. with vigorous shaking. Approximately 1.5 ml of the culture was poured off into an Eppendorf tube and collected by centrifugation in an Eppendorf centrifuge for at least 1 minute; the remainder of the culture was stored at 4° C. and served as a genetic stock. The media above the bacterial pellet was aspirated off and the pellet was suspended by vortexing in 100 $\mu$l of a cold, freshly prepared solution of 50 mM glucose, 10 mM EDTA, 25 mM Tris-HCl (pH 8.0), 4 mg ml$^{-1}$ lysozyme. This mixture was incubated at room temperature for 5 minutes. Then 200 $\mu$l of a cold, freshly prepared solution composed of 0.2N NaOH and 1% SDS was added to each tube, mixed gently by inversion, and put on ice for 5 minutes. To this mixture was added 150 $\mu$l of a cold, freshly prepared solution containing 6 ml of 5M potassium acetate, 1.15 ml of glacial acetic acid, 2.85 ml distilled water. The contents were gently mixed on a vortex mixture and this mixture was stored on ice for 5 minutes. The cellular debris was collected by centrifugation in an Eppendorf centrifuge for 10 minutes at 4° C. and the supernatant was extracted one time with phenol/chloroform/isoamyl alcohol (25:24:1). Plasmid DNA and cellular RNA were precipitated from the final aqueous phase with the addition of two volumes of room temperature 100% ethanol. A pellet was collected by centrifugation for 5 minutes at room temperature, the pellet was washed one time with 70% ethanol and then dried briefly. The nucleic acid pellet was then suspended in 50 μl of TE containing 20 μg of DNase-free RNase per ml and incubated for 15-30 minutes at 37° C. to quantitatively eliminate cellular RNA. Aliquots of 10 μl were then cut to completion with EcoRI (approximately 20 units) in a buffer composed of 50 mM NaCl, 100 mM Tris-HCl (pH 7.5), 5 mM $MgCl_2$ at 37° C. for 60 minutes. The restriction enzyme reaction products were fractionated by agarose gel electrophoresis to identify those plasmids which contained the appropriate inserts. Those recombinant plasmids which contained the predicted EcoRI insert were then cut with a second restriction enzyme (usually Pst I) to verify (i) that only a single copy of the insert was contained within the plasmid, and (ii) to score for orientation of the insert DNA with respect to the bacterial promoter. This was accomplished by removing a second 10 μl aliquot from the remaining 40 μl of RNase-digested bacterial nucleic acid and cutting it in a buffer composed of 100 mM NaCl, 10 mM Tris-HCl (pH 7.5), and 10 mM $MgCl_2$ with approximately 20 units of PstI for 60 minutes at 37° C. Again, the restriction enzyme digests were resolved by agarose gel electrophoresis.

EXAMPLE 13

Production of Eimeria-CheY Fusion Proteins

An overnight culture of selected recombinant bacteria was prepared by inoculating 5 mls of broth with a single colony of bacteria. The culture medium was 2×YT (16 g tryptone, 10 g yeast extract, 10 g NaCl/liter) containing ampicillin (50 μg/ml). The overnight culture was used to inoculate 500 mls of 2×YT containing ampicillin. The culture was grown at 37° C. with aeration until mid-log growth was reached ($A_{550}\simeq 0.5$) at which point IPTG was added to a final concentration of 100 μM. The culture was grown for a further 3–4 hours at 37°, chilled on ice, and centrifuged for 15 minutes at 4° C. The cells were washed once with PBS, then the bacteria were collected by centrifugation and were stored frozen at −70° C. until needed. When needed, the bacterial pellets were thawed and suspended in 10 ml of 30 mM Tris-HCl, pH 8.0, 50 mM EDTA and 1 mM phenylmethylsulphonylfluoride (Buffer A). The suspension was sonicated on ice twice, each time for three minutes, using a Branson cell disrupter Model 350 (duty cycle 30, output control 4). The sonicate was clarified by centrifugation at 27000×g for 45 minutes at 4° C. The supernatant fluid constituted the first supernatant. The pellet of insoluble material was washed in 10 ml of buffer A containing 0.1% w/v Triton X100. The suspension was stirred in an ice bath for 30 minutes prior to centrifugation at 27,000×g for 45 minutes and at 4° C. The supernatant fluid is designated the second supernatant. The pellet ($P_2$) was then washed twice in Buffer A and the wash discarded. Pellet (P2) was suspended in 1.0 ml of 6M guanidine-HCl containing 100 mM dithiothreitol and the suspension was incubated for 2 hours at 50° C. The suspension was diluted to 10 mls with 7M urea and was clarified by centrifugation at 27000×g for 45 minutes at 4° C. The supernatant fluid constituted the third supernatant. Different fusion proteins exhibited different solubility properties, some were found predominantly in the first supernatant, some in the second, and some (most commonly) were found in the third.

The SO6-CheY antigen (recombinant A antigen) was found in the first, second, and third supernatant. Material for in vivo testing was prepared from the third supernatant by ion exchange chromatography. A Trisacryl M-DEAE (LKB) column (5 mls) equilibrated in 0.025M Tris-HCl, pH 8.5, 8M urea was prepared. From the third supernatant, a 2 ml sample, containing 12 mg protein, was dialyzed against 100 ml of the above buffer, and was then applied to the column. The column was washed with one column volume of column buffer, prior to step-wise elution with column buffer containing 0.05M, 0.1M, 0.15M, 0.2M, 0.25M, 0.3M, 0 35M, or 0.4M NaCl. Each elution was performed with two column volumes. Eluates were tested for the presence of recombinant protein by SDS-PAGE and Western blotting, using rabbit anti-Fraction V. The SO6/CheY protein was found to elute in the 0.15M and 0.20M NaCl fractions. Fractions were pooled, dialyzed against 50 mM $NH_4CO_3$, and were freeze dried. The yield of protein from a 500 ml culture is approximately 3 mg.

The SO7-CheY fusion protein (recombinant B antigen) was found in the third supernatant. Further purification was obtained by chromatography on hydroxyapatite. A column of hydroxyapatite (6 ml bed volume; BioRad Labs; HPT grade) was equilibrated in 7M urea, and the third supernatant was applied to the column. After washing the column with one bed volume of 7M urea, the flow-through and wash were combined, concentrated to 10 ml on Amicon diafiltration membrane YM10, dialyzed against 50 mM $NH_4HCO_3$, and were freeze dried (including any precipitate that formed). The yield from a 500 ml culture was approximately 35 mg protein.

The SP54-CheY fusion protein (recombinant C antigen) was also found in the third supernatant. Further purification was unnecessary for in vivo testing. The yield of protein in the third super natant from a 500 ml culture was approximately 170 mg.

The SO311-CheY fusion protein (recombinant H antigen) was also found in the third supernatant. Further purification was obtained by chromatography on hydroxyapatite. The column was prepared as described above, and the third supernatant applied. The column was developed with two bed volumes of 7M urea, then 2 bed volumes of 7M urea containing 10 mM, 20 mM, 40 mM, 80 mM, 160 mM or 320 mM sodium phosphate buffer, pH 6.5. Column eluates were tested for the presence of recombinant protein by SDS-PAGE and Western blotting, using rabbit anti-fraction V, rabbit anti-sporozoite serum, or recombinant eluted antibodies. The SO311/CheY protein was found in the 40 mM, 80 mM and 160 mM eluates. These eluates were pooled, concentrated, dialyzed and freeze dried exactly as above. The yield from a 500 ml culture was approximately 5 mg protein.

The SO216-CheY fusion protein (recombinant F antigen) was also found in the third supernatant fluid. No further purification was necessary for in vivo testing. The yield from a 500 ml culture was approximately 30 mg protein.

EXAMPLE 14

Characterization of Recombinant-Derived *E. tenella* Immunogens

Representative *E. tenella* immunogen clones, from Example 9, were subjected to nucleotide sequence analysis utilizing one or two of three standard methodologies. Some sequence analyses were determined using the chemical degradation method of Maxam and Gilbert, Methods in Enzymology, 65 (part 1): 497–559 (1980). More commonly, the nucleotide sequence was determined by the dideoxy chain termination technique, using denatured plasmid templates (plasmid pUC18, containing assorted subsequences of the *E. tenella* cDNAs) as described by Hattori and Sakaki, Analyl. Biochem. 152: 232-238 (1986). The third approach to nucleotide sequence determination was accomplished by subcloning the cDNA insert, or portions of it, into bacteriophage mp18 and sequencing secreted single-stranded recombinant phage templates using the standard dideoxy chain-termination sequencing methodology of Messing, Methods in Enzymology 101: 20-78 (1983). In addition to AMV reverse transcriptase and the Klenow fragment of DNA polymerase I, a modified T7 DNA polymerase has been employed, see Tabor and Richardson, Proc. Nat. Acad. Sci. U.S.A. 84: 4767-4771 (1987).

The amino acid sequences were deduced from the determined nucleotide sequences by combining the following information. Each of the cDNAs, see Example 8, in the phage expression vector λgtII was identified by polyclonal antisera, see Example 2, when expressed as a fusion protein with β-galactosidase. The nature of the covalent attachment of this fusion protein is shown in the following table.

TABLE 5 the orientation of the insert in these three vectors is established. The orientation of the cDNA insert in plasmid, puc 18 and pJC264, or phage, mp18, vectors is accomplished by restriction enzyme mapping, see Example 9. Once asymmetric restriction enzyme recognition sequences are identified within the cDNA insert, insert orientation and transcriptional orientation can be unequivocally assigned when the recognition sequences are similarly predicted by the nucleotide sequence.

Group A clone nucleotide sequences and the resulting Group A immunogen amino acid sequences are exemplified by the representative clone SO67. This clone is entirely contained within the SO6 clone, see Example 9. Of the approximately 870 nucleotides in this clone the first 162 nucleotides starting at the 5' end have been sequenced. The transcriptional orientation and therefore the correct reading frame can be deduced unambigiously based upon the location in the nucleotide sequence of restriction enzyme recognition sequences which are predicted by restriction enzyme mapping of the CheY-SO67 recombinant plasmid. The nucleotide sequence and the resulting 53N-terminal amino acid sequence is shown in the following table.

TABLE 6

N-Terminal Nucleotide And Deduced Amino Acid Sequence of Group A Immunogen SO67

| 10 | 20 | 30 | 40 | 50 |
|---|---|---|---|---|
| T TTA TTC | CTT CGA TGC | CTG GCG GCG | TTG TTC ATC | ATG TTC ATC | ACG AGG CGC | CTT CTG |
| Leu Phe | Leu Arg Cys | Leu Ala Ala | Leu Phe Ile | Met Phe Ile | Thr Arg Arg | Leu Leu |
|   |   |   | 10 |   |   |   |

| 60 | 70 | 80 | 90 | 100 | 110 |
|---|---|---|---|---|---|
| CTG CTG | CGA TTC ACC | GTT CCT ACC | GTG CTT TGC | TGC TGC AGC | AGC AGC ANG | TGC TCG |
| Leu Leu | Arg Phe Thr | Val Pro Thr | Val Leu Cys | Cys Cys Ser | Ser Ser XXX | Xys Ser |
| 20 |   |   | 30 |   |   |   |

| 120 | 130 | 140 | 150 | 160 |
|---|---|---|---|---|
| TCG ANG | NAG AGC GCC | GGG GCA GCA | GAA GCA GCA | GCA GCA GCA | GCT CG |
| Ser XXX | XXX Ser Ala | Gly Ala Ala | Glu Ala Ala | Ala Ala Ala | Ala |
| 40 |   |   |   | 50 |   |

An additional 221 nucleotide sequence has been obtained from the 3' end of the clone, see table 7 below, but the reading frame has not been deduced.

TABLE 7

3' Nucleotide Sequence of Group A Immunogen SO67

| 1 | CGAGTGGCTG | GTTGACACCG | GCAGGGTCTT | CGCCGGCGGC | GTTGCTAGCA | TAGCCGACGG |
| 61 | CTGCCGGCTC | TTCGGAGCAG | CAGTGGAGGG | CGAGGGCAAC | GCTGGGAAGA | ACTCGTCAAG |
| 121 | ACCAACTACC | AAATTGAAGT | CCCCCAGGAA | GACGGAACCT | CCATTTCAGT | GGATTGCGAC |
| 181 | GAGGCGGAGA | CTCTGCGGCA | GGCGGTGGTG | GACGGCCGCG | C | |

EcoRI Cloning Site

```
         EcoRI
B-galactosidase  |  E. tenella

5'       GCG GAA TTC       3'
         Ala Glu Phe
```

This junction (and reading frame, cloning site) at the EcoRI cleavage site, is regenerated in each subsequent cloning event involving the entire cDNA irrespective of the subcloning vector, pUC18, mp18 or pJC264. Consequently, the reading frame can be unequivocally identified and the nucleotide sequence translated once Group B clone nucleotide sequence and the resulting Group B immunogen amino acid sequence are exemplified by the representative clone SO7. The reading frame can be deduced unambiquously by correlating the position of restriction enzymes sites asymmetrically located within the cDNA with the location of their respective recognition sequences as predicted by the nucleotide sequence analysis. All 957 nucleotides in this clone have been sequenced. The nucleotide sequence and the amino acid sequence up to the termination codon at base 713 are shown in the following table.

TABLE 8

Nucleotide And Deduced Amino Acid Sequence of Group B Immunogen SO7

| 10 | 20 | 30 | 40 | 50 |

TABLE 8-continued

Nucleotide And Deduced Amino Acid Sequence of Group B Immunogen SO7

| | | | | | | |
|---|---|---|---|---|---|---|
| T CTC GCC<br>  Leu Ala<br>60 | CCA ACT TTT<br>Pro Thr Phe<br>70 | TCC CCC GCG<br>Ser Pro Ala<br>80 | CTC CGC AGC<br>Leu Arg Ser<br>      10<br>90 | AGC AGC AGC<br>Ser Ser Ser<br>100 | AGC AGC AGC<br>Ser Ser Ser<br>110 | AGC AGC<br>Ser Ser |
| AGC AAA<br>Ser Lys<br>20<br>120 | ATG GCA GAC<br>Met Ala Asp<br>130 | CTC TTC AGC<br>Leu Phe Ser<br>140 | GGA CTC GTG<br>Gly Leu Val<br>      30<br>150 | GGC GGC GTC<br>Gly Gly Val<br>160 | GTC GGC GCT<br>Val Gly Ala<br>170 | GTT GCT<br>Val Ala |
| GCA GCA<br>Ala Ala<br>40 | GAT TTG CCT<br>Asp Leu Pro<br>180 | GCG GAG GGC<br>Ala Glu Gly<br>190 | GAG AGG GCC<br>Glu Arg Ala<br>200 | CCC CGC CCC<br>Pro Arg Pro<br>50<br>210 | GCC CCC GGC<br>Ala Pro Gly<br>220 | ACT GCC<br>Thr Ala |
| TGG ACT<br>Trp Thr<br>230 | TGC TGC TGC<br>Cys Cys Cys<br>60<br>240 | AGC AAA CTG<br>Ser Lye Leu<br>250 | CAA GAA GGG<br>Gln Glu Gly<br>260 | GCC CGC GAG<br>Ala Arg Glu<br>70<br>270 | CTG GAG GGT<br>Leu Glu Gly<br>280 | TTT GTG<br>Phe Val |
| CAG CAG<br>Gln Gln<br>290 | CTG AGT TTT<br>Leu Ser Phe<br>80<br>300 | GTT GCA GGG<br>Val Ala Gly<br>310 | AAG CTG GCC<br>Lys Leu Ala<br>320 | TGC TGC CTG<br>Cys Sys Leu<br>90 | CGG GTG GGG<br>Arg Val Gly<br>330 | GCG GAG<br>Ala Glu<br>340 |
| CAG CTG<br>Gln Leu | GCG CGC TGC<br>Ala Arg Cys<br>100<br>350 | GCT GCG GAG<br>Ala Ala Glu<br>360 | GGG CGG CTG<br>Gly Arg Leu<br>370 | CCC AGC AGC<br>Pro Ser Ser<br>380 | AGC AGC AGC<br>Ser Ser Ser<br>110<br>390 | AGC AGC<br>Ser Ser<br>400 |
| TGC TGC<br>Cys Cys | GCG CTG CTG<br>Ala Leu Leu<br>410 | CAG CTC GAG<br>Gln Leu Glu<br>120<br>420 | AAG CAG GAC<br>Lys Gln Asp<br>430 | CTC GAG CAG<br>Leu Glu Gln<br>440 | AGC CTC GAG<br>Ser Leu Glu<br>130<br>450 | GCC GGC<br>Ala Gly |
| AAG CAG<br>Lys Gln<br>460 | GGC GCG GAG<br>Gly Ala Glu<br>470 | TGC CTC TTG<br>Cys Leu Leu<br>140<br>480 | AGG AGC AGC<br>Arg Ser Ser<br>490 | AAA CTG GCC<br>Lys Leu Ala<br>500 | CTC GAG GCC<br>Leu Glu Ala<br>150<br>510 | CTC CTC<br>Leu Leu |
| GAG GGG<br>Glu Gly<br>520 | GCC CGC GTT<br>Ala Arg Val<br>530 | GCA GCA ACG<br>Ala Ala Thr<br>160 | CGG GGT TTG<br>Arg Gly Leu<br>540 | CTG CTG GTC<br>Leu Leu Val<br>550 | GAG AGC AGC<br>Glu Ser Ser<br>560 | AAA GAC<br>Lys Asp<br>170<br>570 |
| ACG GTG<br>Thr Val | CTG CGC AGC<br>Leu Arg Ser<br>580 | ATT CCC CAC<br>Ile Pro His<br>590 | ACC CAG GAG<br>Thr Gln Glu<br>180<br>600 | AAG CTG GCC<br>Lys Leu Ala<br>610 | CAG GCC TAC<br>Gln Ala Tyr<br>620 | AGT TCT<br>Ser Ser<br>190 |
| TTC CTG<br>Phe Leu<br>630 | CGG GGC TAC<br>Arg Gly Tyr<br>640 | CAG GGG GCA<br>Gln Gly Ala<br>650 | GCA GCG GGG<br>Ala Ala Gly<br>200<br>660 | AGG TCT CTG<br>Arg Ser Leu<br>670 | GGC TAC GGG<br>Gly Tyr Gly<br>680 | GCC CCT<br>Ala Pro |
| GCT GCT<br>Ala Ala<br>210<br>690 | GCT TAC GGC<br>Ala Tyr Gly<br>700 | CAG CAG CAG<br>Gln Gln Gln<br>710 | CAG CCC AGC<br>Gln Pro Ser<br>220<br>720 | AGC TAC GGG<br>Ser Tyr Gly<br>730 | GCG CCC CCC<br>Ala Pro Pro<br>740 | GCC TCC<br>Ala Ser |
| AGC CAG<br>Ser Gln<br>230 | CAG CCC TCC<br>Gln Pro Ser<br>750 | GGC TTC TTC<br>Gly Phe Phe<br>760 | TGG TAG CCC<br>Trp —<br>770 | TGC AGC AGC<br>780 | AGC AGC AGC<br>790 | AGC AGC<br>800 |
| AGC AGC GCG<br>810 | GGC GGC AGC<br>820 | CGC GGC GGG<br>830 | GCC GGG GCG<br>840 | CCG CTG CAG<br>850 | CAA CAG<br>860 | |
| CCG nnn CGG<br>870 | CTA GCG CCG<br>880 | CGG AGC ACT<br>890 | CGC AGG GAA<br>900 | CTC CAC AGG<br>910 | CAG CGG<br>920 | |
| GAG AGC<br>AGC AGG GAC<br>930 | GAG AAG CAG<br>940 | GTC ATG TAG<br>950 | CGC AGG CAG | CAG CGC CAG | CTG CAG | |
| CAG CAG | CAG CAG CAG | CAG CAG CAG | CAG CAG CAG | CTC CTG CAC | CG | |

Group C clone nucleotide sequence and the resulting Group C immnunogen amino acid sequence are exemplified by the representative clone SP54, see Example 9. This clone is entirely contained within the SP59 clone, see Example 9. Of the approximately 700 nucleotides in this clone the first 157 nucleotides starting at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping of the CheY-SP54 recombinant plasmid. The nucleotide sequence and the resulting 52 amino acid sequence is shown in the following table.

fore the appropriate reading frame can be unequivocally deduced by correlating restriction enzyme recognition sequences in the nucleotide sequence with their asymmetric location predicted by restriction enzyme mapping. The nucleotide sequence and the resulting 61 amino acid sequence is shown in the following table.

TABLE 10

N-Terminal Nucleotide and Deduced Amino Acid Sequence of Group H Immunogen SO311

| | 10 | 20 | 30 | 40 | 50 | |
|---|---|---|---|---|---|---|
| C CTG GCC<br>Leu Ala | ACA GGG CTC<br>Thr Gly Leu | CTG TTC GCC<br>Leu Phe Ala | AAC AGC CTG<br>Asn Ser Leu<br>10 | CTG CGA CAT<br>Leu Arg His | GGA TCT GTC<br>Gly Ser Val | AGA GTG<br>Arg Val |
| 60 | 70 | 80 | 90 | 100 | 110 | |
| GCA CAT<br>Ala His<br>20 | TGT GAA TGC<br>Cys Glu Cys | AAT TCT GTG<br>Asn Ser Val | CGG GTC TCT<br>Arg Val Ser<br>30 | TGC GGC CGC<br>Cys Gly Arg | TGC TCA CTT<br>Cys Ser Leu | CGC CAC<br>Arg His |
| 120 | 130 | | 140 | 150 | 160 | 170 |
| GAA AGT<br>Glu Ser<br>40 | CAA CCC CAG<br>Gln Pro Gln | GGC TAT GCA<br>Gly Tyr Ala | AGC TGG ATT<br>Ser Trp Ile | CAG AGT ATA<br>Gln Ser Ile<br>50 | CAA GGC CGA<br>Gln Gly Arg | AAC TTC<br>Asn Phe |
| | 180 | | | | | |
| AAT GCG<br>Asn Ala | CGA GCT C<br>Arg Ala<br>60 | | | | | |

An additional 283 nucleotide sequence has been obtained from the 3' end of the clone, see table below, but the reading frame has not been deduced. Linker nucleotides are included in positions 1-8.

TABLE 9

N-Terminal Nucleotide and Deduced Amino Acid Sequence of Group C Immunogen SP54

| | 10 | 20 | 30 | 40 | 50 | |
|---|---|---|---|---|---|---|
| C GCG GAA<br>Ala Glu | TCC GCA GAC<br>Ser Ala Asp | ACT GCT GAG<br>Thr Ala Glu | ATC CGC GTG<br>Ile Arg Val<br>10 | CCC GTG GGG<br>Pro Val Gly | GCC ACT GTG<br>Ala Thr Val | GTG GTG<br>Val Val |
| 60 | 70 | 80 | 90 | 100 | 110 | |
| CGG CTT<br>Arg Leu<br>20 | CAG AGC GTT<br>Gln Ser Val | GGG GGC TAC<br>Gly Gly Tyr | AGG CCA GTG<br>Arg Pro Val<br>30 | TTG GTG AGT<br>Leu Val Ser | GCC CAG AGT<br>Ala Gln Ser | GGG GCT<br>Gly Ala |
| 120 | 130 | | 140 | 150 | | |
| GTG GGC<br>Val Gly<br>40 | CTC TCC GAG<br>Leu Ser Glu | CTT TCC CAG<br>Leu Ser Gln | GCT TCC CCC<br>Ala Ser Pro | AGT TCG GCC<br>Ser Ser Ala<br>50 | | |

TABLE 11

3' Terminal Nucleotide Sequence of Group H Immunogen SO311

| 1 | GAATTCGGGT | TATCCACATC | ACGGTGGACG | TCTGATTTAG | CGGAGGAGGT | ATGAACCCTC |
|---|---|---|---|---|---|---|
| 61 | AGAGCCAGCC | CAGTAGGAAG | CATTCATCCA | TCTTGGTCTT | TGCTCCCACA | GACGGTGCAG |
| 121 | GATTTCGAGG | AGAGAGTGTA | TCATTCCTCT | CAGTGTTGGG | ATGACATTCT | CAGATGCGCG |
| 181 | CATCACGTAA | TGATAGCCAT | TCCTGCTCCA | GTCGGAAGCT | ATGTCCTGAC | TCTGGAGAGC |
| 241 | AGCATTTCGG | CGTGATACTT | GAGCTTGTCA | GAGATAGCCA | GCTGCTTCGA | G |

Group H clone nucleotide sequence and the resulting Group H immunogen amino acid sequence is exemplified by the representative clone SO311, see Example 9. Of the approximately 650 nucleotides in this clone, the first 185 nucleotides starting at the 5' end have been sequenced. The transcriptional orientation and there- Group F clone nucleotide sequence of the Group F immunogen is exemplified by the representative clone SO216, see Example 9. The approximately 487 nucleotides, including eight linker nts at each end, have been sequenced. The sequence is given in the followed table.

TABLE 12

Nucleotide Sequence of Group F Immunogen SO216

| 1 | GAATTCGGGC | AGAAAACAAT | TACTGAAAGA | CGGAGGGAAA | GTGTCTCGCC | GGCAAAGTTA |

TABLE 12-continued

| Nucleotide Sequence of Group F Immunogen SO216 | | | | | |
|---|---|---|---|---|---|
| 61 AGCGAACGGA | CTGATTTGGA | AATAGGGTCT | TGCTGCGCAA | ACGAATGCTG | CAAATGCATC |
| 121 CCAAAGCGGT | ACCGCGATGG | ATCAGCAAGA | AAAACNCCTC | AGTGAAACGA | TAGGAGCTGA |
| 181 TGCCGAAGTC | CGCACAGCAT | GATCTATGTC | TCATCGCTGC | TGAGTTAGCT | ACTGAGGCCA |
| 241 CACGGAAGGA | GTGCTTTAGT | TGTAGTTCTT | GAGGTCTTCT | ACGTGTACGG | CATAGTCGAT |
| 301 GCTAGGGAAA | CGAACAAGAG | GGGCACCAGG | TGACGACTCG | TCGATGTCAG | CATGGAAGCC |
| 361 AGCAGCCGCC | AGGACAGGCG | TCAAGGCAAC | GAGTGGGAGT | AAAGCTTCAA | TGGCGCTGTC |
| 421 TTTGCTGACT | TTCGAGATCC | AGGAGGTCTC | GGCAGACTCG | CTGACGGACT | GGAGCAGCTC |
| 481 CGAATTC | | | | | |

The molecular weights of the primary in vitro translation products directed by mRNA specific for immunogens A, B, C and H were determined. In vitro translation of mRNA extracted from unsporulated oocysts, sporulating oocysts and sporozoites was performed using the rabbit reticulocyte cell free translation system, with either $^{35}S$ methionine or $^3H$-leucine as the incorporated indicator isotope. Specific in vitro translation products were immuno-precipitated using monospecific antibodies, prepared as described in Example 6. The protocol for in vitro translation was as described in the technical bulletin from Promega Biotec (according to manufacturer's instructions) and for immunoprecipitation as in Taylor et al., Mol. Biochem. Parasitol. 10:305-318 (1983). The group A primary translation product recognized by monospecific antibody has a molecular weight of 24 kilo Daltons (kD). The major group B immunogen from clone SO7 has a molecular weight of 28 kD while the minor immunogens have molecular weights of 170, 24, 22, 16, and 12kD. The additional minor specifically immunoprecipitable in vitro translation products were detectable when $^3H$-leucine was used as the labelled precursor amino acid. The 170 kD plus 22 kD minor immunogens were also detectable with $^{35}S$-methionine. The major 28 kD immunogen was detectable only when $^3H$-leucine was used as the precursor amino acid. The molecular weight for the group C immunogen was not determined. The major group H immunogen from clone SO311 has a molecular weight of 28kD while the minor immunogens have molecular weights of 48, 38, 33, 16, 13, 12 and 10 kD. The additional minor specifically immuno-precipitable in vitro translation products were detectable when $^{35}S$-methionine was used as the labelled precursor amino acid. The major 28 kD immunogen was detecable when both $^{35}S$-methionine and $^3H$-leucine were used.

The specific mRNAs extracted from unsporulated and sporulating oocysts and/or sporozoites of *E. tenella*, Example 5, were sized by Northern blot analysis according to the method of Maniatis et al., Molecular Cloning, A Laboratory Manual, Cold Spring Harbor Laboratory, Cold Spring Harbor, N.Y., pg. 202 (1982) and the method described in Transfer and Immoblization of Nucleic Acids to S & S Solid supports, published by Schleicher and Schuell, Inc., pgs. 16–19 (1987). The mRNA complimentary to group A clone SO67, was 2.15±0.13 kilobases (kb), to group B, clone SO7, was 1.23±0.22 kb; to group C, clones SP54 and SP59, was 1.12±0.08 kb; and to group H, clone SO311, was 0.98±0.07 kb.

Molecular weights and isoelectric points of *E. tenella* immunogens were also determined. Molecular weights were determined by analytical sodium dodecyl sulphate (SDS) polyacrylamide gel electrophoresis (PAGE) of samples prepared from sporulated oocysts and/or sporozoites of *E. tenella*, followed by transfer to nitrocellulose and immunodetection by Western Blotting as described in Example 6. Isoelectric points were determined by Western blotting of two dimensional gels of samples as described above. The dimensional gels were run according to the procedure of O'Farrell, J. Biol. Chem. 250: 4007-4021 (1975). Antibodies for both procedures were prepared as stated in Examples 2 and 6. The results are shown in the following table.

TABLE 13

| Molecular Weight and Isoelectric Points of Native *E. tenella* Immunogens | | | |
|---|---|---|---|
| Immunogen group | Representative clones | Molecular weight (kD) | Isoelectric point |
| A | SO6, SO67 | 24 | 3.65 |
| B | SO7 | 27–28<br>22, 19, 18, 14,<br>12, 9, 6 | 5.1–6.3 |
| C | SP54, SP59 | 21–22 | n.d. |
| H | SO311 | 28, 18<br>27, 24, 23, 17<br>14, 12, 9 | 6.65 |
| F | SO216 | 26–29 | n.d. |

The predominant B immunogen is characterized as a diffuse doublet of 27-28 kD on SDS-PAGE with the minor immunogens appearing as faint bands suggesting some sharing of antigenic determinants within *E. tenella*. The 27-28 doublet produces multiple spots on isoelectric focusing, in the range between pH 5.1 and 6.3. The pIs of the faint additional bands detected by Western blotting were not determined.

EXAMPLE 15

Induction Of Protection To Challenge With *E. tenella* By Recombinant Derived *E. tenella* Immunogens Broiler pullets were immunized three times via the intramuscular route on days 2, 9 and 16 days of age with samples containing 10 μg of the specific recombinant fusion immunogen, from Example 13, in phosphate buffered saline absorbed on alum, 0.4% final concentration, in a total volume of 0.12 ml per dose per bird. The immunogen-alum complex was prepared by the procedure of Weir, Handbook of Experimental Immunology, Blackwell Scientific Publications London, pg. A3.11 (1978). Experimental and control birds were challenged at day 23, seven days after the final immunization, with an oral inoculation of from 5 to $30 \times 10^3$ sporulated oocysts, an amount sufficient to yield a mean lesion score of at least 2.5 in non-immunized controls at 30 days of age. Seven days after challenge the chickens were killed and the severity of the lesions in the ceca was determined according to the method of Johnson and Reid, Exp. Parasitol. 28:30-36 (1970). Representative examples of the results are shown in Tables 14–18.

TABLE 14
Protection Of Chickens Against Coccidiosis With Group A Immunogen SO67-CheY

| Challenge dose (× 10⁻³) | Immunized infected | Non-Immunized infected |
| --- | --- | --- |
| 5 | 2.18 | 3.41 |
| 10 | 2.57 | 3.57 |
| 15 | 1.78 | 3.44 |

TABLE 15
Protection Of Chickens Against Coccidiosis With Group B Immunogen SO7-CheY

| Challenge dose ($\times 10^{-3}$) | Immunized infected | Non-Immunized infected |
| --- | --- | --- |
| 10 | 1.41 | 3.00 |
| 20 | 1.28 | 3.43 |
| 30 | 1.34 | 3.38 |

TABLE 16
Protection Of Chickens Against Coccidiosis With Group C Immunogen SP54-CheY

| Challenge dose ($\times 10^{-3}$) | Immunized infected | Non-Immunized infected |
| --- | --- | --- |
| 5 | 1.71 | 3.38 |
| 10 | 1.68 | 3.00 |
| 15 | 1.93 | 3.22 |

TABLE 17
Protection Of Chickens Against Coccidiosis With Group H Immunogen SO311-CheY

| Challenge dose ($\times 10^{-3}$) | Immunized infected | Non-Immunized infected |
| --- | --- | --- |
| 10 | 2.03 | 2.97 |
| 15 | 2.00 | 3.32 |

TABLE 18
Protection Of Chickens Against Coccidiosis With Group F Immunogen SO216 CheY

| Challenge dose ($\times 10^{-3}$) | Immunized infected | Non-Immunized infected |
| --- | --- | --- |
| 10 | 1.50 | 2/16 |
| 15 | 1.30 | 2.72 |
| 20 | 1.25 | 2.89 |

These results show that recombinant *E. tenella* immunogens A, B, C, H, and F can be used to immunize two-day-old chickens against coccidiosis. Three intramuscular inoculations provide a high level of protection against the disease as indicated by the absence of severe lesion development in immune birds after a normally virulent infection.

EXAMPLE 16
Isolation Of The Native Form Of The B Immunogen From *Eimeria tenella*

A suspension of $1 \times 10^9$ sporulated oocysts of *E. tenella* in 20 ml of phosphate buffered saline (PBS) containing 0.1 mM phenylmethylsulfonylfluoride (PMSF) was sonicated in an ice bath for a total of 10 minutes, in 2.5 minute bursts using a Branson Sonic Power Co. Sonifier Cell Disrupter 350 (duty cycle 30%, output control 4). The sonicate was centrifuged at $27,000 \times g$ for 30 minutes at 4° C. The pellet was washed 3 times in 40 ml PBS/0.1 mM PMSF, and was recovered by centrifugation as described above. The washed pellet was resuspended in 60 ml of 5M guanidine HCl/0.5M Tris-HCl, pH 8.6, and 400 mg dithiothreitol. Reduction was allowed to proceed for 3 hours at 20° C. with mild agitation. Insoluble debris was removed by centrifugation as described above. The supernatant fluid, containing reduced and solubilized B antigen was concentrated by ultrafiltration (Ultrafilter PM 10, Amicon Corp.) to 20 ml, and iodoacetic acid (400 mg) was added. The pH was readjusted to 8.6 by the addition of 3M Tris base, and carboxymethylation was allowed to proceed for 60 minutes at 20° C. in the dark. The reaction mixture was then dialyzed for 48 hours against 0.05M $NH_4HCO_3$/0.1 mM PMSF/0.02% sodium azide. With the removal of guanidine-HCl, some insoluble material formed which was subsequently removed by centrifugation as described above. The cleaned supernatant was then concentrated to 12 ml by ultrafiltration, as described above. The concentrate was then applied to a sizing column of Sephacryl S-200 ($87 \times 2.5$ cm) equilibrated in 0.05M $NH_4HCO_3$, 0.1% Zwittergent 3-12 (Calbiochem), 0.02% sodium azide. A total of $120 \times 4.5$ ml fractions were collected, at a flow rate of 25 ml/hour. Effluent fractions were monitored at 280 nm, and the elution of the B immunogen was monitored by Western blotting, initially using rabbit anti sporozoite antiserum, and subsequently with a rabbit antiserum to the SO7/CheY protein. Fractions containing the B antigen (47–57) were pooled, concentrated to 10 ml, and were reapplied to the column. The column was eluted and monitored as before. Pooled fractions were concentrated to a volume containing approximately 0.5 mg protein/ml. The total yield was 5.8 mg.

SDS gel analysis showed a single homogenously pure protein of 30 kD±3 kD, which on Western blot analysis was reactive with both rabbit anti-sporozoite antiserum and rabbit anti SO7-CheY.

The immunogenic activity of this sample of B antigen purified from *E. tenella* was measured as described in Example 15. Two day old broiler pullets were immunized three times via the intramuscular route on days 2, 9 and 16 with samples containing 10 μg of the purified native B immunogen absorbed on alum (0.4% final concentration). The immunogen alum complex was prepared by the procedure of Weir, Handbook of Experimental Immunology, Blackwell Scientific Publications, London, pg. A3-11 (1978). Experimental and control birds were challenged at day 23, seven days after the final immunization with an oral inoculation of from $5-15 \times 10^3$ sporulated oocysts. Seven days after challenge, the chickens were killed and the severity of the lesions in the ceca was determined according to the method of Johnson and Reid, Exp. Parasitol, 28, 30-36 (1970). Results are presented as mean cecal lesion scores for groups of eight birds and are shown in the following table.

TABLE 19
Protection of Chickens Against Coccidiosis With Native Group B Immunogen

| Challenge dose ($\times 10^{-3}$) | Immunized infected | Non-Immunized infected |
| --- | --- | --- |
| 5 | 1.36 | 3.41 |
| 10 | 1.64 | 3.57 |

TABLE 19-continued

Protection of Chickens Against Coccidiosis
With Native Group B Immunogen

| Challenge dose ($\times 10^{-3}$) | Immunized infected | Non-Immunized infected |
|---|---|---|
| 15 | 1.54 | 3.44 |

An alternative method of purifying the B immunogen from *E. tenella* is by affinity chromatography, using the antibody to the SO7-CheY protein. For this purpose, two affinity columns were prepared, one using serum from a rabbit removed prior to immunization with the SO7-CheY antigen (prebleed column), and one using antiserum from the same rabbit immunized with the SO7-CheY antigen, using the immunization regime described in Example 2. The SO7-CheY immunogen was prepared as described in Example 13. The immunoglobulin IgG fraction was prepared from 4 ml of each serum, using the method of Corthier et al., J. Immunol. Met., 66, 75-79 (1984). For each column, 15 mg of IgG was coupled to 0.5 gm of Sepharose-Protein A (Sigma), using the method of Schneidert et al., J. Biol. Chem. 257, 10766-10769 (1982). Coupling efficiency was between 75-95%. For immunoaffinity purification, approximately 5 mg of the reduced, carboxymethylated extract, prepared as described above (with no purification by gel filtration), on 0.1M borate buffer, pH 8.1, 0.5M NaCl, 0.02% NaN$_3$, 0.1 mM PMSF, was applied to the prebleed column equilibrated in the same buffer. The column was washed with 3 ml of column buffer, and the combined column flow-through and washes were then applied to the anti SO7/CheY column equilibrated in the same buffer. The column was washed with 10 ml of column buffer, prior to elution with 3M NaSCN. The eluate was dialyzed for 48 hours versus 0.05M NH$_4$HCO$_3$, prior to freezing. A total of approximately 50 μg protein was recovered in the final eluate.

The immunogenic activity of this affinity purified B antigen from *E. tenella* was tested as described in Example 15. Two day old broiler pullets were immunized three times via the intramuscular route on days 2, 9 and 16 with samples containing approximately 0.3 μg of the immunoaffinity purified Group B immunogen absorbed on alum (0.4% final concentration). The immunogen-alum complex was prepared by the procedure of Weir, Handbook of Experimental Immunology, Blackwell Scientific Publications, London, pg. A3-11 (1978). Experimental and control birds were challenged at day 23, seven days after the final immunization, with an oral inoculation of from 10-30×10$^3$ sporulated oocysts. Seven days after challenge, the chickens were killed, and the severity of the lesions in the ceca was determined according to the method of Johnson and Reid, Exp. Parasitol. 28, 30-36. Results are presented as mean cecal lesion scores for groups of eight birds and are shown in the following table.

TABLE 20

Protection of Chickens Against Coccidiosis
With Native Group B Immunogen

| Challenge Dose ($\times 10^{-3}$) oocysts | Immunized Infected | Non-Immunized Infected |
|---|---|---|
| 10 | 1.41 | 3.00 |
| 20 | 1.44 | 3.43 |
| 30 | 1.59 | 3.38 |

Samples of the expression vector pJC264 containing the DNA for the various *E. tenella* immunogens have been deposited in a host *Escherichia coli*, JM83 or JM109, under the Budapest Treaty in the American Type Culture Collection, 12301 Parklawn Drive, Rockville, Md. 20852, U.S.A. On Nov. 4, 1987, samples of the expression vector containing clones SO7, SO6, SP54 and SO311 were deposited and were given accession numbers 67577, 67559, 67556 and 67558 respectively. On Dec. 19, 1987, a sample of the expression vector containing clone SP59 was deposited and given accession number 67594. On Jan. 8, 1988, a sample of expression vector containing clone SO216 was deposited and given accession number 67600.

What is claimed is:

1. An expression vector comprising the lac promoter DNA sequence directly and operably linked to a truncated CheY DNA sequence comprising the 264 N-terminal nucleotides of the CheY gene with said CheY sequence terminating with an EcoRI restriction enzyme site.

2. The expression vector of claim 1 designated pJC264.

3. The expression vector of claim 1 wherein said expression vector allows the expression of CheY fusion proteins in *Escherichia coli*.

4. A method for producing CheY fusion proteins comprising:
   a. cultivating in a medium a *Escherichia coli* transformed with the vector of claim 1 wherein said vector contains foreign DNA operably linked to the CheY DNA;
   b. disrupting the *Escherichia coli* and collecting the fusion protein;
   c. purifying the fusion proteins so that they are free of *Escherichia coli* proteins.

* * * * *